United States Patent [19]

Villa et al.

[11] Patent Number: 5,284,966
[45] Date of Patent: Feb. 8, 1994

[54] INTERMEDIATES FOR THE STEREOCHEMICAL INVERSION OF (2S, 3S)-2-AMINO-3-PHENYL-1,3-PROPANEDIOLS INTO THEIR (SR,3R) ENANTIOMERS

[75] Inventors: Marco Villa, Milan; Claudio Giordano, Monza; Silvia Cavicchioli, Bellinzago Lombardo; Silvio Levi, Milan, all of Italy

[73] Assignee: Zambon Group S.p.A., Vicenza, Italy

[21] Appl. No.: 992,747

[22] Filed: Dec. 18, 1992

Related U.S. Application Data

[63] Continuation of Ser. No. 599,881, Oct. 19, 1990, Pat. No. 5,202,484.

[30] Foreign Application Priority Data

Oct. 22, 1989 [IT] Italy ................. 22075 A/89

[51] Int. Cl.$^5$ ................. C07C 381/00; C07C 323/00; C07C 321/00
[52] U.S. Cl. ........................... 560/9; 560/17; 560/250; 564/185; 564/212; 564/219; 564/302; 564/304; 548/215
[58] Field of Search ............ 560/9, 17, 250; 564/185, 212, 219

[56] References Cited

U.S. PATENT DOCUMENTS

| | | | |
|---|---|---|---|
| 2,483,885 | 10/1949 | Crooks | 564/185 |
| 2,538,763 | 1/1950 | Crooks | 564/185 |
| 2,699,451 | 1/1955 | Moersch | 564/185 |
| 2,717,268 | 9/1955 | Rebstock | 564/212 |
| 2,721,207 | 10/1955 | Bambas | 564/212 |
| 2,742,500 | 4/1956 | Gregory et al. | |
| 2,744,136 | 5/1956 | Gregory | 564/185 |
| 2,759,970 | 8/1956 | Suter | 564/212 |
| 4,632,940 | 12/1986 | Chiarino et al. | |
| 4,638,003 | 1/1987 | Chiarino et al. | |

FOREIGN PATENT DOCUMENTS

| | | |
|---|---|---|
| 0014437 | 8/1980 | European Pat. Off. |
| 130633 | 1/1985 | European Pat. Off. |
| 0130633 | 1/1985 | European Pat. Off. |
| 1228146 | 7/1985 | Italy |
| 1190407 | 10/1985 | Italy |
| 1196434 | 7/1986 | Italy |
| 1186716 | 12/1987 | Italy |
| 1223563 | 12/1987 | Italy |

OTHER PUBLICATIONS

V. Horak et al., Communications, "Oppenauer Oxidation of 2-Acylamino-1-aryl-1,3-propanediols; A New Method for Racemization of an Optically Active Diastereoisomer", Oct. 1984, pp. 839-840.

C. Giordano et al., Tetrahedron Letters, "New Strategy for Racemization of 2-Amino-1,3-Propanediols, Key Intermediates for the Synthesis of Antibiotic Drugs", vol. 29, No. 43, pp. 5561-5564, 1988.

Giordano et al., J. Org. Chem., 1991, vol. 56, No. 21, pp. 6114-6118.

Eliel, "Second-Order Asymmetric Transformation", pp. 62-63 & 38-41, 1980.

Jerry March, Advanced Organic Chemistry, 3rd ed., pp. 102-109, 527-529, 796-798, 1057-1060 (1982).

Primary Examiner—John M. Ford
Assistant Examiner—Matthew V. Grumbling
Attorney, Agent, or Firm—Oblon, Spivak, McClelland, Maier & Neustadt

[57] ABSTRACT

Intermediates for transforming (2S,3S)-2-amino-3-phenyl-1,3-propanediols into their (2R,3R)-enantiomers are described. The final compounds are useful intermediates for the synthesis of antibiotics like Chloramphenicol, Thiamphenicol and Florfenicol.

3 Claims, No Drawings

INTERMEDIATES FOR THE STEREOCHEMICAL INVERSION OF (2S, 3S)-2-AMINO-3-PHENYL-1,3-PROPANEDIOLS INTO THEIR (SR,3R) ENANTIOMERS

This is a continuation application of copending application Ser. No. 07/599,881, filed on Oct. 19, 1990 now U.S. Pat. No. 5,202,484.

The present invention concerns a process for the conversion of (2S,3S)-2-amino-3-phenyl-1,3-propanediols into their corresponding (2R,3R)-enantiomers.

Many 2-amino-3-phenyl-1,3-propanediols are useful as intermediates for the synthesis of antibiotics like Chloramphenicol (Merck Index, X Ed., No. 2035, page 289) and Thiamphenicol (Merck Index, X Ed., No. 9140, page 1332). Often, their synthesis is accompanied with discard products having a wrong configuration.

Said compounds may be collected under the following formula

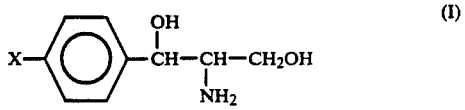
(I)

wherein: $X=H$, $NO_2$, $CH_3S$, $CH_3SO$ or $CH_3SO_2$.

The compounds of formula I having the (2R,3R) configuration are useful for the synthesis of the above cited antibiotics while the enantiomers I (2S,3S) are generally discard products of the industrial synthesis.

The compounds of formula I wherein $X=NO_2$ are known as threo-(2R,3R)-micamine and (2S,3S)-micamine while those in which $X=CH_3S$ as threo-(2R,3R)-thiomicamine and (2S,3S)-thiomicamine.

A further compound under development having antibiotic activity is Florfenicol (European Patent No. 14437—Schering Co.) which has a structure analogous to that of Thiamphenicol wherein instead of the primary hydroxy group there is a fluorine atom.

The synthesis of Florfenicol, (2S,3R)-3-(4-methylsulphonylphenyl)-3-hydroxy-2-dichloroacetamido-1-fluoro-propane, may be carried out starting from (2R,3R)-thiomicamine (see also European patent application No. 130,633-Zambon S.p.A.).

Some of the processes for the synthesis of Chloramphenicol or Thiamphenicol comprise the preparation of a racemic mixture of the isomers threo (2R,3R)+(2S,3S) of micamine or of thiomicamine.

The desired threo (2R,3R) isomer is then separated by a resolution process and is converted into the antibiotic compound by N-dichloroacetylation and, in the case of Thiamphenicol, also by oxidation of the $CH_3S$ group into $CH_3SO_2$.

The isomer threo-(2S,3S), on the contrary, is a discard product of the synthesis which must be eliminated thus increasing the cost of the desired isomer.

Some processes have been studied which allow the racemization of the (2S,3S)-intermediate, i.e. to convert them into a 1:1 mixture of the threo (2R,3R) and (2S,3S)-isomers [Tetrahedron Letters, 29, 5561, (1988) and references cited therein].

From these racemates the (2R,3R)-isomer must be separated and the (2S,3S)-isomer must be racemized again.

The process for racemization of aminodiols thus becomes cumbersome.

So, it would be useful to have available a process allowing the stereochemical inversion of the discard products of the synthesis of Chloramphenicol and Thiamphenicol, by transforming directly the above reported intermediates (formula I) having (2S,3S)-configuration into their (2R,3R) enantiomers useful for the synthesis of the compounds having antibiotic activity.

However, to our knowledge, there has never been previously described a process allowing said double inversion.

SUMMARY OF THE INVENTION

We have now found and it is the object of the present invention, a multi-step process with a low cost and high total yields, which allows one to convert the above reported intermediates having (2S,3S)-configuration into the corresponding compounds having (2R,3R)-configuration.

The process for the inversion of both the stereogenic centres, the object of the invention, comprises the following steps which will be described in detail in the following.

A) Protection of the amino group and of the hydroxy in position 3 of the (2S,3S)-3-phenyl-2-amino-1,3-propanediols of formula

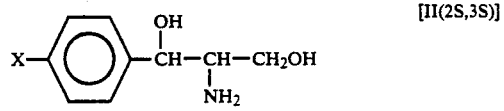
[II(2S,3S)]

wherein $X=H$, $NO_2$, $CH_3S$, $CH_3SO$ or $CH_3SO_2$.

B) Oxidation of the $CH_2OH$ group to formyl or formyl derivative, carboxy or carboxy-derivative and epimerization of the carbon atom alpha to the oxidized group.

C) Restoring of the primary alcoholic function by reduction of the oxidized group.

D) Removal of the protective groups introduced in step A and epimerization of the benzylic centre in position 3.

DETAILED DESCRIPTION OF THE PREFERRED EMBODIMENT

In view of the fact that the process of the invention has particular importance when applied to the synthesis of Thiamphenicol and, as below reported, of Florfenicol and because of the fact that both these compounds may be prepared from (2R,3)-thiomicamine or from intermediates of the process, the process will be illustrated giving particular relevance to its application to the inversion of the stereogenic centres of (2S,3S)-thiomicamine.

It has to be understood that, whenever not differently specified, what will be illustrated for thiomicamine stands also for the other intermediates of formula I.

In the following description by the term lower alkyl or lower alkoxy we mean a $C_1$-$C_4$ alkyl or $C_1$-$C_4$ alkoxy, by the term carboxy derivative we mean an alkoxycarbonyl group wherein the alkoxy has 1-4 carbon atoms, an aminocarbonyl group or a mono or dialkylaminocarbonyl group wherein alkyl has 1-4 carbon atoms, by formyl derivative we mean acetals or hemiacetals or hydrates of the aldehyde group and oximes or hydrazones thereof, by the term acyl we mean an acyl radical of a lower carboxylic acid having 1-5 carbon atoms optionally substituted by 1 or 2 halogen atoms, in particular dichloro-acetyl, or of a benzoic acid optionally substituted by chlorine or bromine atoms or by lower alkyl groups.

STEP A

The protection of the hydroxy group in position 3 and of the nitrogen atom is carried out, by procedures per se known, by the introduction of two different protecting groups (III-A) as well as by the contemporaneous protection of the hydroxy and nitrogen by formation of an oxazolidine derivative (III-B).

Protection of type A: is carried out by transforming the hydroxy in 3 into an ether or into an ester and by acylation of the NH$_2$ group. Both the reactions are carried out by per se conventional methods.

The transformation in ether is that presently preferred and can be conveniently carried out by heating thiomicamine in alcohol (e.g. methanol or ethanol) in the presence of an excess of mineral acid (e.g. sulphuric acid).

The reaction affords in practically quantitative yield the ether derivative of configuration 2S,3S (e.g. 3-phenyl-3-ethoxy-2-amino-1-propanol).

The acylation of the nitrogen atom is carried out by using an acylating agent selected from carbonic or carboxylic acid halides, anhydrides or esters according to conventional techniques for the preparation of amides.

By an economic point of view it is preferred to use acetyl chloride or acetic anhydride thus obtaining the corresponding acetamide.

It is clear to the man of the art how the hydroxy and the amino groups may be protected by a variety of methods compatible with the functional groups of the molecule and that this does not represent a meaningful variation of the object of the invention.

For a compendium of the known methods for the protection of hydroxy and amino groups reference is made to T. W. Greene "Protective Groups in Organic Synthesis", J. Wiley and Son—New York, chapters 2 and 7 respectively.

The two above reported reactions afford the protected (2S,3S)-thiomicamine of formula

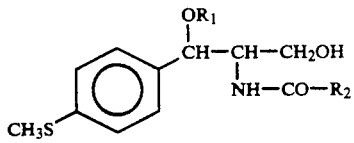

wherein R$_1$ represents a lower alkyl or acyl and R$_2$ represents hydrogen, a lower alkyl, dichloromethyl, phenyl, alkoxy or benzyloxy group.

Preferably, in the compounds of formula III-A, R$_1$ represents methyl or ethyl and R$_2$ methyl.

By operating according to a completely analogous procedure, the analogs of the compounds of formula III-A derived from micamine or from the other intermediates of formula I may be prepared.

Protection of type B: it consists in preparing a derivative of N-acyl-1,3-oxazolidine by a heterocyclic ring closure between the nitrogen and the hydroxy in position 3.

The oxazolidine is preferably prepared by first protecting the primary hydroxy group as ester and the nitrogen as amide by conventional techniques.

Preferably, the acylating agent of the hydroxy (ester) and the nitrogen (amide) will be the same.

The reaction is carried out by reacting thiomicamine with an excess of acylating agent (chloride, anhydride or ester of a carboxylic or carbonic acid) to obtain by first a diester in which both the hydroxy groups of the molecule have been esterified. By basic catalysis the diester is transformed to the desired product of formula

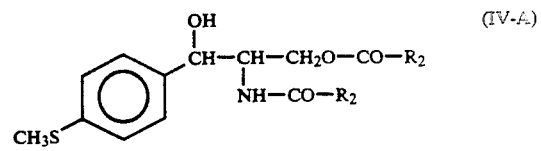

wherein the R$_2$S, equal to or different from each other, have the same meanings above reported.

The preparation of the compounds of formula IV-A has already been described in Italian patent No. 1,186,716 (Zambon S.p.A.) which concerns a process for the racemization of 2S,3S-threo-thiomicamine. For economical reasons it is preferred to use as acylating agent an acetic derivative thus obtaining the compound IV-A wherein both the R$_2$ are methyl.

In a practical embodiment the reaction is carried out in a single step by reacting (2S,3S)-thiomicamine with 2 moles of acetyl chloride and 2 moles of a non-nucleophilic organic base (e.g. Et$_3$N) in an inert diluent such as a chloroorganic aliphatic or aromatic solvent (e.g. methylene chloride, 1,2-dichloroethane, dichlorobenzene).

Alternatively, it is possible to prepare the N-acyl-derivative of thiomicamine by reaction with an acyl chloride or chloroformiate and then to esterify the primary hydroxy by conventional methods.

The thiomicamine protected both as ester on the primary hydroxy and as amide on the NH$_2$ is then transformed in an oxazolidine derivative of formula

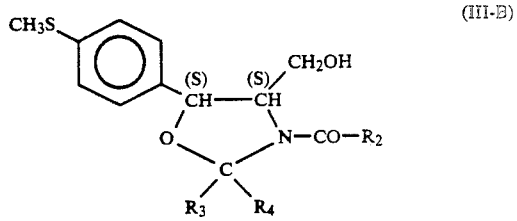

wherein R$_2$ has the above reported meanings, R$_3$ and R$_4$ equal to or different from each other, represent hydrogen atoms, lower alkyls, phenyls, lower alkoxy or R$_3$ and R$_4$ together are an oxygen or sulphur atom or a tetra or pentamethylene chain.

The preparation of some of the compounds of formula III-B has been described in European patent application No. 130,633 (Zambon S.p.A.) which concerns a process for the preparation of Florfenicol.

The preparation of the compounds of formula III-B from protected thiomicamine comprises the condensation with an aldehyde or an acetal thereof (to obtain the compounds of formula III-b wherein R$_3$=R$_4$=H or R$_3$=H and R$_4$=alkyl or aryl) or with a ketone or a ketal thereof (for R$_3$ and R$_4$=alkyl or R$_3$ and R$_4$ together=tetra or pentamethylene chain), or with an orthoformate (for R$_3$=H and R$_4$=alkoxy), with a chloroformate, a dialkylcarbonate, a thiocarbonate (for R$_3$ and R$_4$ together=oxygen or sulphur atom).

Specific examples of compounds suitable for being condensed with the protected thiomicamine to afford the oxazolidine are the following: formaldehyde, acetaldehyde, propionaldehyde, benzaldehyde and their acetals, acetone, diethylketone, methyl-ethylketone, acetophenone, cyclopentanone, cyclohexanone and their ketals, trimethylorthoformate, trimethylorthoformate, alkyl chloroformate, diethylcarbonate and diethylthiocarbonate.

In order to avoid the introduction in the molecule of a new asymmetric center, it is preferred to prepare an oxazolidine wherein $R_3 = R_4$. Accordingly, formaldehyde and symmetrical ketones like acetone, diethylketone, cyclopentanone and cyclohexanone or their ketals are preferred.

For economy reasons it is preferred to use formaldehyde, acetone or its dimethylketal (2,2-dimethoxy-propane).

The condensation reaction is carried out in the presence of a catalytic amount of an acid, e.g. a sulphonic acid or sulphuric acid by avoiding, however, an excess of acid in the mixture, at a temperature comprised between room temperature and 100° C., in an inert solvent.

The reaction affords the oxazolidine wherein the $CH_2OH$ group is protected as ester according to the protection previously introduced on the thiomicamine.

The oxazolidine of formula III-B is obtained by deprotecting said hydroxy by treatment with an alkaline base in an alcoholic solvent optionally in the presence of water.

Alternatively, the preparation of oxazolidine III-B may be carried out by treating directly thiomicamine with an agent which can afford the oxazolidine, as cited above, which may also act as solvent (e.g. by using acetone both as reactant and solvent) under azeotropic distillation of the water formed in the reaction (e.g. in the presence also of toluene).

Thereby, the oxazolidine of formula

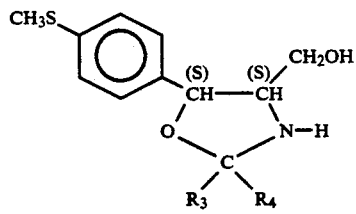

(IV-B)

wherein $R_3$ and $R_4$ have the above reported meanings, is obtained.

The N-acylation of compound IV-B by an acyl halide or ester in the presence of a base or by an anhydride (e.g. acetic anhydride) provides the oxazolidine III-B.

Also in this case, for the same reasons above reported, it is preferred that $R_3$ and $R_4$ be equal to each other, e.g. $R_3 = R_4 = CH_3$.

From the above reported reactions, thiomicamine protected on both the hydroxy in position 3 and the nitrogen in the form of an open chain (III-A) or cyclic (III-B) derivative, is thus obtained.

For convenience, we collect under a single formula (formula III) the two above described kinds of protection

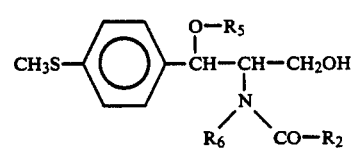

[III, (2S, 3S)]

wherein $R_2$ has the above reported meanings, $R_5$ represents a lower alkyl or acyl and $R_6$ a hydrogen atom or $R_5$ and $R_6$ together are the group $C(R_3)(R_4)$—wherein $R_3$ and $R_4$ have the above reported meanings.

By operating in an analogous way, the compounds of formula III derived from micamine and from the other intermediates of formula I can be prepared.

STEP B

It comprises the oxidation of the $CH_2OH$ group of the compounds of formula III and the epimerization of the carbon atom in alpha to the oxidized group.

The two steps have been collected in a single step because, depending on the reaction conditions of the oxidation step, it is possible to have a contemporaneous epimerization.

Thus, the $CH_2OH$ group of compounds III is oxidized to formyl, carboxy or carboxy derivative like, preferably, methoxycarbonyl or ethoxycarbonyl.

The oxidation reaction is preferably carried out by using reactants that do not oxidize the $CH_3S$ group present on the aromatic ring.

For this purpose, reference is made to J. March, "Advanced Organic Chemistry", 3rd Edition, J. Wiley & Son—New York, for a compendium of the methods for oxidation of a primary alcohol to aldehyde or carboxy derivatives, and to the following papers:

A. J. Mancuso, D. Swern, Synthesis, 165 (1981)
D. F. Taber et al., J. Org. Chem., 52, 5621, (1987)
J. C. Collins, Tetrahedron Lett., 3363, (1968)
T. Miyazawa et al., J. Org. Chem., 50, 1332, (1985)
D. H. Hunter et al., J. Org. Chem., 53, 1278, (1988)
P. L. Anelli et al., J. Org. Chem., 52, 2559, (1987)
V. Franzen, Organic Synthesis Coll., vol. V, 872
S. Mukaiyama et al., Bull. Chem. Soc. Japan, 54, 2221, (1981)

or references cited therein.

The Oppenhauer or the Swern-Moffat oxidations are useful for the purpose even if any oxidant able to afford the desired chemoselectivity may be equally useful.

The experiments carried out according to the Swern conditions (dimethylsulphoxide, oxalyl chloride followed by triethylamine at low temperature) gave satisfactory results.

Alternatively, chlorine and dimethylsulphide or $P_2O_5$ and dimethylsulphoxide and $Et_3N$, or $CrO_3$ and pyridine or chlorine and pyridine, trichlorocyanuric acid and pyridine, N-chloroamides and dimethylsulphide or methyl-phenylsulphide, a benzenesulphonic acid chloride with dimethylsulphoxide and triethylamine, were used as reactants and afforded analogous results.

The oxidation of the hydroxymethyl group of compound III to carboxy or alkoxycarbonyl is carried out by known procedures too.

Thereby are obtained the compounds of formula

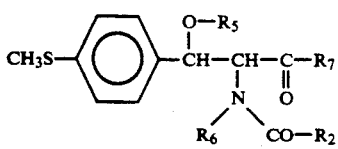

[V, (2R, 3S)]

wherein $R_2$, $R_5$ and $R_6$ have the above reported meanings and $R_7$ represents a hydrogen atom, hydroxy, alkoxy, preferably methoxy or ethoxy.

From the compound of formula V wherein $R_7=H$ ($COR_7=$formyl) it is possible to prepare the carbonyl derivatives like oximes, hydrazones, acetals, hemiacetals or hydrates, these latters may be prepared also during the oxidation phase.

The preparation of the amides of the compounds of formula V ($R_7=$amino, mono o dialkylamino) is carried out by known methods starting from the compounds of formula I wherein $R_7=$hydroxy or alkoxy.

Even if generally it is not necessary, the aim for transforming the formyl in a carbonyl derivative or the carboxy in amide is that of modifying the solubility in the different solvents in order to make easier the separation of the products.

The carbonyl derivatives may be then retransformed into formyl or directly reduced to hydroxymethyl according to the subsequent step. Preferably, the preparation of the compounds of formula V wherein $R_7$ is different from hydrogen will be carried out by first preparing by oxidation the compounds wherein $R_7$ is alkoxy and from these, when desired, the compounds wherein $R_7$ is hydroxy, amino, mono or dialkylamino.

The preferred compounds of formula V are those in which $R_7$ is a hydrogen atom and they are a further object of the present invention.

We recall that, according to nomenclature conventions, the replacement of the $CH_2OH$ group by a $CO-R_7$ group modifies the denomination of the configuration of the carbon atom in position 2 (from S to R) but this does not mean that its initial absolute configuration is changed.

The presence of the formyl, alkoxycarbonyl or of the other above cited groups in the compounds V allows the epimerization of the alpha carbon both under acidic and basic conditions.

Therefore, this allows to obtain a mixture of compounds V having configuration 2R,3S and 2S,3S. This latter one is the desired compound in which the center in position 2 has inverted its configuration.

We have surprisingly found that when the epimerization is carried out by using non-nucleophilic bases such as tertiary amines [in particular triethylamine; 1,5,7-triazacicyclo-[4,4,0]-dec-5-ene; 1,8-diazabicyclo-[5,9,0]-undec-7-ene; or still, more preferably, diazabicyclooctane (DABCO)] preferably in a non-protic medium, an equilibrium mixture of compounds V (2R,3S) and (2S,3S) is obtained from which, optionally by seeding V (2S,3S), the desired compound precipitates and contemporaneously the mixture of compounds V in solution re-equilibrates.

Thereby, the desired compound V (2S,3S) with high diastereomeric purity and in up to 90% yield is obtained.

This is a quite rare reaction, called "second order asymmetric transformation", which to our knowledge finds few precedents in carbohydrate chemistry.

The same reaction may also be carried out with analogous results by operating in the absence of solvents. In view of the high yield in V (2S,3S) the reaction crude may be used for the subsequent reaction without isolating the product, provided that the epimerization catalyst (acid or base) is eliminated or neutralized.

Obviously, as an alternative, it is possible to separate the oxidized product also not under equilibrating conditions (e.g. by transforming the formyl into a carbonyl derivative which modifies the solubility in the reaction medium).

As above mentioned, the reaction conditions for the oxidation of the hydroxymethyl group in compounds III may afford a more or less advanced degree of epimerization. In such case, e.g. by terminating the Swern oxidation with triethylamine, the subsequent treatment for withdrawing the isomer V (2S,3S) from the equilibrium will be carried out.

By operating in an analogous way it is possible to prepare the analogs of compound V (2S,3S) derived from micamine or from the other intermediates of formula I.

Obviously, in this case, the problem of undesired oxidations is decreased thus broadening the choice of the oxidants and allowing an easier synthesis of the compounds in which the $CH_2OH$ group is oxidized.

STEP C

It consists in the reduction of the $CO-R_7$ group of compound V (2S,3S) to hydroxymethyl in order to obtain a compound of formula

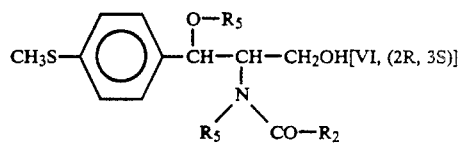

[VI, (2R, 3S)]

wherein $R_2$, $R_5$ and $R_6$ have the above reported meanings.

We further recall that the change in the configuration of the carbon atom in 2 (from 2S in compound V to 2R in compound VI) is due only to nomenclature conventions and does not correspond to an inversion of configuration.

The reduction of the $CO-R_7$ group to hydroxymethyl must be carried out under conditions which do not result in an epimerization and which do not reduce other functional groups.

In particular, strongly acidic and basic conditions must be avoided. It is thus necessary to use a substantially neutral reducing agent and/or to operate in the presence of a buffer.

A reducing agent suitable for industrial use is sodium borohydride in alcohol. In view of the fact that the industrial product might contain sodium hydroxyde, it is preferred to use also a buffer, a calcium salt (e.g. $CaCl_2$) or a weak acid.

However, we have observed that when in compound V [(2S,3S)+(2R,3S)] $R_7$ is hydrogen and the reduction is carried out in alcohol without added buffer, the reaction of the selected stereoisomer [V, (2S,3S)] to afford the desired stereoisomer [VI, (2R,3S)] is faster thus allowing and increase in its diastereomeric purity. This fact is meaningful in particular when the compounds V and VI are oxazolidines.

For a compendium of the known reduction methods reference is made to J. March above cited.

By operating according to these conditions the reduction is highly selective and affords compound VI (2R,3S) in high yield and purity.

By operating an analogous way the analogs of compound VI (2R,3S) derived from micamine or from the other intermediates of formula I are prepared.

STEP D

It consists in the deprotection of the hydroxy in 3 and of the amino in 2 and in the epimerization of the benzylic carbon atom in 3.

The reactions have been collected under a single step because they may be carried out in the same reaction vessel, because the deprotection, when carried out according to the below reported experimental conditions, already affords the epimerized product and also because the epimerization reaction may precede that of deprotection. Step D may be conveniently carried out by heating, at a temperature comprised between 20° and 100° C., a suspension of compound VI (2R,3S) in water containing 1-3 equivalents of a strong acid for each mole of compound VI.

Suitable acids are hydrochloric, hydrobromic, sulphuric, methanesulphonic and p.toluenesulphonic acid.

We have surprisingly found that under these conditions the 2R,3S-thiomicamine is in equilibrium with the desired 2R,3R-enantiomer. Further studies allowed to find out other experimental conditions, below illustrated, which allow this quite useful equilibrium to occur.

In a short time compound VI (2R,3S) is hydrolized to N-acyl-aminodiol and in a longer time the epimerization of the carbon in position 3 occurs. This important observation allows to realize also an alternative to the process which will be illustrated in the following.

At the equilibrium the ratio between thiomicamine 2R,3S and 2R,3R is about 30:70.

By cooling the equilibrium solution the (2R,3R)-thiomicamine, i.e. the product of double inversion with respect to the starting product, precipitates in the form of a salt with the acid present.

By treatment of this salt with a base (2R,3R)-thiomicamine is obtained as enantiomerically pure free base.

An acid is added to the mother liquors and they are heated for equilibrating the diastereomer (2R,3S) with that (2R,3R).

The cycle is repeated until thiomicamine terminates.

Alternatively, further acid and further compound VI (2R,3S) may be added to the mother liquors thus repeating both the hydrolysis and the equilibration.

An alternative procedure for carrying out step D consists in carrying out the hydrolysis (D-2) and perform subsequently the equilibration of the (2R,3S)-thiomicamine thus obtained.

The epimerization of the benzylic centre may be carried out according to the following experimental conditions:

in acidic water, thereby isolating the salt of thiomicamine with the selected acid or thiomicamine as free base after alkalinization of the reaction mixture after epimerization;

in a carboxylic acid (acetic or propionic) as solvent, optionally in the presence of a strong acid; ester or amides of thiomicamine are isolated depending on the used concentration and amount of acid. Free thiomicamine is obtained by mild hydrolysis;

in an alcoholic medium (methanol or ethanol) in the presence of at least a stoichiometric amount of a strong acid. In this case, if desired, an ether derivative of thiomicamine with the used alcohol may be isolated (3-alkoxy-analog of thiomicamine) from which free thiomicamine is obtained by mild hydrolysis of the ether group. Alternatively, the hydrolysis may be carried out in the reaction mixture by a simple dilution of the epimerization mixture with water.

in a presently preferred embodiment, in an anhydride with a strong acid, in particular, in acetic anhydride and hydrated p.toluenesulphonic acid, followed by mild basic hydrolysis. It is likely that the reaction involves the formation of cyclic intermediates and also of acyloxy derivatives.

In fact, starting from (4R,5S)-2,2-dimethyl-3-acetyl-4-hydroxymethyl-5-(4-methylthiophenyl)-1,3-oxazolidine as compound VI and by operating in the above conditions, the intermediates (4R,5S)-2,2-dimethyl-3-acetyl-4-acetoxymethyl-5-(4-methylthiophenyl)-1,3-oxazolidine and (4R,5R)-2-methyl-3-acetyl-4-acetoxymethyl-5-(4-methylthiophenyl)2-oxazoline were isolated.

The above reported reactions afford (2R,3R)-thiomicamine i.e. compound I (2R,3R) wherein $X=CH_3S$. In an analogous way step D is carried out for obtaining the compound of formula I (2R,3R) wherein $X=H$.

When it is desired to prepare the compounds of formula I having configuration (2R,3R) in which $X=CH_3SO_2$, $CH_3SO$ or $NO_2$ it is necessary to carry out step D in a different way.

The inversion of the carbon atom in 3 (benzylic centre) is carried out by an $S_N2$ nucleophilic substitution.

The compound VI (2R,3S) is firstly subjected to a mild hydrolysis for deprotecting the benzylic hydroxy while leaving the nitrogen protected as amide. The $CH_2OH$ group is protected as an ester by reaction with an acyl halide in the presence of a base thus obtaining a compound of formula IV-A but having 2R,3S configuration. This is then treated with thionyl chloride in dichloromethane and the reaction product is subjected to a complete hydrolysis. Also in this case, it is likely that the reaction involves the formation of an oxazoline intermediate.

An alternative procedure consists in treating with a base directly the compound VI (2R,3S) i.e. without having deprotected the benzylic hydroxy. The desired product is then obtained by deprotecting the functional group by mild hydrolysis in an acidic medium.

The above described process thus allows, through the four steps A, B, C and D, the inversion of both the asymmetric carbon atoms of molecules of formula II, but also starting from erythro forms.

This result is possible thanks to a double inversion which is realized by means of two sequential reciprocal inductions. In the first inversion the benzylic carbon atom induces the preferential configuration of the carbon in position 2 bound to the nitrogen and to the oxidized group, in the subsequent induction the carbon atom having R configuration in position 2 induces configuration R during the equilibration of the benzylic carbon atom.

It is worth noting how the reactions involved in the process afford high yields and need cheap reactants of normal industrial use.

Moreover, as cited at the beginning of the specification, the process is easily suitable for the preparation of (2S,3R)-3-(4-methyl-thiophenyl)-3-hydroxy-2-amino-1-fluoro-propane and of the analog 3-(4-methylsulphonyl-phenyl)-derivative which are useful intermediates for the synthesis of Florfenicol (European patent 14437).

It must be again recalled that by nomenclature conventions the presence of the fluorine atom instead of the hydroxy causes a change in the denomination of the carbon atom in position 2 (from R to S) but it does not correspond to a variation in the configuration.

In European patent application No. 130633 (Zambon S.p.A.) a process for the preparation of Florfenicol is described, said process comprises the replacement of the hydroxy by a fluorine atom in cyclic intermediates among which also oxazolidines and 1,3-oxazolidine-2-ones.

The process object of the invention may be applied to the synthesis of Florfenicol by the following procedure.

After having carried out the inversion of the asymmetric centre in 2 and the reduction of the formyl (or alkoxycarbonyl) group to hydroxymethyl, i.e. after having performed steps A, B and C, the $CH_2OH$ group of the reaction product [VI (2R,3S)] is transformed into $CH_2F$. The transformation is carried out according to what described in European patent application No. 130633 above cited and preferably by a mesylation of the hydroxy and reaction of the mesylated product with KF in polyglycol.

The compound of formula

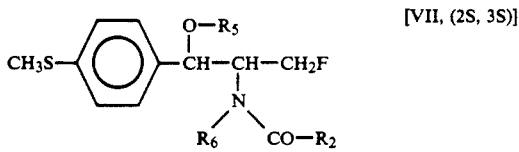

[VII, (2S, 3S)]

wherein $R_2$, $R_5$ and $R_6$ have the above reported meanings, is thus obtained.

By carrying out step D of the process on compound VII, the inversion of the benzylic centre and the deprotection from the protective groups is realized thus obtaining the (2S,3R)-3-(4-methylthiophenyl)-3-hydroxy-2-amino-1-fluoro-propane from which, by a known method Florfenicol is prepared. It is likely that the intermediates of the process comprise oxazoline derivatives as above discussed.

Also in this case it is possible to perform the process starting from 4-methylsulphonyl-derivatives (II, $X=CH_3SO_2$) or to prepare the corresponding intermediate by oxidation of the $CH_3S$ group to $CH_3SO_2$ in compound VII.

The epimerization of the benzylic centre in 3 will be then performed by an $S_N2$ nucleophilic substitution as above reported.

As above mentioned, in the specific cases of the compounds of formula Ia II wherein $X=H$ or $CH_3S$ it is possible to perform the general process above described by inverting the order of some of the steps. It has been in fact surprisingly observed that by treatment with carboxylic acids optionally in the presence of a strong acid or with acidic water, the compounds of formula II wherein $X=H$ or $CH_3S$ undergo an inversion of configuration at the benzylic carbon atom in 3 which affords a thermodynamic equilibrium mixture wherein the compound II (2S,3R) may be separated in the form of triacyl-derivative (diester-amide) and this by hydrogenolysis affords the compound II (2S,3R) or its corresponding amide.

This allows to realize an alternative of the process object of the invention wherein the inversion of the benzylic centre in 3 is not performed during step D but precedes step A. Said process may be summarized as follows:

D-1) Epimerization of the benzylic centre in 3 to obtain compound
II wherein $X=H$ or $CH_3S$ having configuration (2S,3R).
A) Protection of the amino and hydroxy group in position 3 of the product from step D-1.
B) Oxidation of the $CH_2OH$ group to formyl, carboxy or carboxy-derivative and epimerization of the carbon atom in alpha to the oxidized group.
C) Restoring of the primary alcoholic function by reduction of the oxidized group.
D-2) Deprotection from the protective groups introduced in step A.

Step D-1 is carried out, as above reported, by treating compound II (2S,3S) wherein $X=H$, $CH_3S$ with an acid in epimerization conditions.

By a practical point of view this is realized by heating a suspension of compound II in water in the presence of a strong acid or by heating a solution of compound II in acetic or propionic acid optionally in the presence of a strong acid.

Step D-1, thus, is completely analog to step D in its feature concerning the epimerization of the benzylic centre in 3, the only difference being the fact that the inversion of the carbon atom in 2 bound to the amino group did not yet occur.

Compound II (2S,3R) (X=H, $CH_3S$) thus obtained is then reacted according to steps A, B and C which afford the inversion of the carbon atom in 2.

Steps A, B and C are carried out exactly as above reported.

Obviously, having already inverted the configuration of the carbon atom in 3, the configuration of same in the intermediates III-A, III-B, IV-A, IV-B, V and VI is inverted.

Step D-2 than follows and is carried out according to what described for step D in its feature concerning the removal of the protective groups introduced in step A.

Also in this case, obviously, the hydrolysis reactions must be performed in mild conditions in order to avoid epimerization of the stereogenic centres.

The use of acidic water as reaction medium is again useful provided that the temperature and the reaction time be sufficient for carrying out the two hydrolysis but do not give substantial epimerization.

In a practical embodiment, which is presently the preferred for the inversion of the two stereogenic centres of thiomicamine, the process object of the invention comprises the following steps:
condensation of 2S,3S-thiomicamine with acetone to afford (4S,5S)-5-(4-methylthiophenyl)-4-hydroxymethyl-2,2-dimethyl-1,3-oxazolidine and N-acetylation of same;
oxidation of the hydroxymethyl group to formyl and epimerization of the carbon atom in 4 of the oxazolidine;
reduction of the formyl to hydroxymethyl by $NaBH_4$;
treatment with an acid in an aqueous medium for epimerizing the carbon atom adjacent to the phenyl and for deprotecting the (2R,3R)-thiomicamine;
followed by the recycling of the mother liquors of the last reaction.

In a still more preferred embodiment, the last step is carried out by using acetic anhydride with hydrated p.toluenesulphonic acid.

This last reaction is quite new and unexpected.

It is worth noting that the process object of the invention take advantage of some per se known reactions together with some new and unexpected reactions and results.

Certain reactions like protection and deprotection of functional groups, oxidation of primary alcohols to carbonyl or carboxy derivatives and their reduction to alcohols are certainly per se known.

However, they are generally known as far as isolated functional groups are concerned while the starting products and intermediates of the process contain contemporaneously various functional groups with several possibilities of interference.

For example, in the protection and oxidation steps there are three different functional groups to discriminate, i.e. the primary hydroxy, the benzylic hydroxy and the amino group. Moreover, when in the starting product and intermediates $X=CH_3S$, the sulphur atom too might be involved in the oxidation processes.

The starting product and the intermediates contain two adjacent asymmetric carbon atoms on a total of three carbon atoms of the aliphatic chain moreover, as a consequence, four stereoisomers exist among which it is necessary to discriminate for the realization of the process.

A further difficulty which had to be overcome was that of finding a synthetic strategy, and realize it in practice, by which could allow the epimerization of the carbon atom in 2 bound to the amino group while keeping unaltered the configuration of the benzylic carbon in 3 and subsequently the epimerization of the benzylic carbon atom while keeping unaltered the configuration of the carbon atom in position 2.

The global strategy of the process was realized in practice thanks to certain unexpected results like the finding of the quite unusual second order asymmetric transformation of which take advantage step B.

The epimerization of step D, to our knowledge, finds no precedent in the literature and the preferred conditions (acetic anhydride and hydrated p.toluenesulphonic acid) are quite new too.

The most valuable merit of the process consists in having realized the found strategy by using rather unexpensive and industrially available reactants and by using reaction conditions which are easily industrialized.

With the aim to better illustrate the present invention the following example are given.

EXAMPLE 1

Preparation of
threo-(2S,3S)-3-(4-methylthiophenyl)-3-hydroxy-2-acetamido-1-acetoxy-propane (Compound 1)

Triethylamine (104.5 g; 1.03 mol) was added at 25° C. in 15 minutes to a suspension of threo-(2S,3S)-2-amino-3-(4-methylthiophenyl)-1,3-propanediol [(2S,3S-thiomicamine] (100 g; 0.469 mol) in methylene chloride (500 ml) kept under mechanical stirring and under nitrogen, and then acetyl chloride (81.1 g; 1.03 mol) was added dropwise in 2 hours. During the addition the reaction temperature rose up to 40° C. At the end of the addition the reaction mixture was cooled at 25° C. and kept under stirring for 2 hours.

The reaction mixture was then poured into a 5% sodium bicarbonate solution (500 ml); after separation of the phases, the aqueous phase was extracted with methylene chloride (200 ml).

The combined organic phases were dried over sodium sulphate and evaporated to dryness under vacuum.

Crude compound 1 (140.2 g) (titre 67.4%) was obtained.

By column chromatography (silica gel, eluent ethyl acetate:methanol=98:2) an analytically pure sample was obtained.

$^1$H-NMR (300 MHz, CDCl$_3$): δ (ppm): 1.91 (s, 3H); 2.08 (s, 3H); 2.47 (s, 3H); 4.06 (dd, J=5.5 Hz, J=10.4 Hz, 1H); 4.26 (dd, J=10.4 Hz, J=6.2 Hz, 1H); 4.30 (dddd, J=5.5; 6.2; 4.0; 8.1 Hz, 1H); 4.80 (d, J=4.0 Hz, 1H); 6.01 (d, J=8.1 Hz, 1H); 7.13 (AA'BB'sy, Δν=20.9 Hz, 4H).

I.R. (KBr): 3450 cm$^{-1}$, 3380 cm$^{-1}$, 1750 cm$^{-1}$, 1655 cm$^{-1}$, 1635 cm$^{-1}$.

M.p.=98.5°-99.5° C.

EXAMPLE 2

Preparation of
(4S,5S)-5-(4-methylthiophenyl)-4-acetoxymethyl-3-acetyl-2,2-dimethyl-1,3-oxazolidine (Compound 2) and
of
(4S,5S)-5-(4-methylthiophenyl)-4-hydroxymethyl-3-acetyl-2,2-dimethyl-1,3-oxazolidine (Compound 3)

2,2-Dimethoxy-propane (355.4 g; 3.41 mol) and monohydrated p-toluenesuphonic acid (4.5 g; 0.02 mol) were added to a solution of the crude compound 1 (Example 1) (140 g) in acetone (275 ml) kept under stirring and under nitrogen at 25° C.

The solution was heated under reflux for 1.5 hours and cooled to 25° C. Potassium carbonate (3.5 g; 0.02 mol) was added under stirring to the solution. After 30 minutes the suspension was filtered and evaporated under vacuum to give an oily residue (161.3 g) (compound 2).

HPLC titre=53.2%

By column chromatography (silica gel, eluent ethyl acetate) an analytically pure sample was obtained.

$^1$H-NMR (300 MHz, DMSO): δ (ppm): 1.48 (s, 3H); 1.51 (s, 3H); 2.04 (s, 3H); 2.10 (s, 3H); 2.48 (s, 3H); 4.26 (m, J=4.34 Hz, 2H); 4.38 (m, Δν=13.9 Hz, 1H); 5.05 (d, J=4.0 Hz, 1H); 7.34 (AA'BB'sy, Δν=42.5 Hz, 4H).

I.R. (CCl$_4$): 2980 cm$^{-1}$, 1748 cm$^{-1}$, 1665 cm$^{-1}$, 1390 cm$^{-1}$, 1220 cm$^{-1}$.

An 85% potassium hydroxide solution (31.7 g) in methanol (150 ml) was added in 1 hour into a solution of the crude compound 2 (161 g) in methanol (500 ml) kept under mechanical stirring under nitrogen at 15° C.

The reaction mixture was evaporated to dryness and the residue was collected by methylene chloride (400 ml) and a 2% ammonium chloride solution (200 ml).

The aqueous phase was extracted with methylene chloride (100 ml); the combined organic phases were washed with water, dried and evaporated to dryness. A crude product (108.5 g) (HPLC titre 73.7%) was obtained which was crystallized from ethyl acetate (160 ml) to give compound 3 (50.9 g; 173 mmol).

$^1$H-NMR (300 MHz, DMSO): δ (ppm): 1.47 (s, 3H); 1.50 (s, 3H); 2.06 (s, 3H); 2.47 (s, 3H); 3.55 (ddd, J=5.7; 11.5; 4.0 Hz, 1H); 3.61 (ddd, J=5.7; 11.5; 6.8 Hz, 1H); 4.06 (ddd, J=3.8 Hz, J=4.0 Hz, J=6.8 Hz, 1H); 5.07 (d, J=3.8 Hz, 1H); 5.24 (t, J=5.7 Hz, 1H); 7.33 (AA'BB'sy, Δν=41.6 Hz, 4H).

$[\alpha]_D^{20}=+16.93°$ (conc. 1.06%, CHCl$_3$)

I.R. (KBr): 3280 cm$^{-1}$, 1630 cm$^{-1}$.
M.p.=142°-145° C.

EXAMPLE 3

Preparation of
(4R,5S)-5-(4-methylthiophenyl)-4-formyl-3-acetyl-2,2-dimethyl-1,3-oxazolidine (Compound 4)

A solution of dimethylsulphoxide (38.2 g; 0.49 mol) in methylene chloride (100 ml) was added to a solution of oxalyl chloride (23.21 g; 0.183 mol) in methylene chloride (100 ml) kept at −60° C. under nitrogen. After 30 minutes a solution of compound 3 (Example 2) (50.9 g; 0.173 mol) in methylene chloride (660 ml) was added. The reaction mixture was kept at −60° C. for 30 minutes, then triethylamine (91.0 g; 0.96 mol) was added at −60° C. under stirring.

The reaction mixture was kept at −60° C. for 15 minutes, then it was heated to 0° C. in 1 hour and poured into a 5% sodium bicarbonate solution (350 ml). The aqueous phase was washed with methylene chloride (100 ml); the combined organic phases were dried over sodium sulphate and evaporated under vacuum to give an oily residue (53.7 g).

Compound 4

Major rotamer (56%)

$^1$H-NMR (300 MHz, CDCl$_3$): δ (ppm): 1.62 (s, 3H); 1.70 (s, 3H); 2.16 (s, 3H); 2.42 (s, 3H); 4.35 (dd, J=8.79-2.91 Hz, 1H); 4.91 (d, J=8.79 Hz, 1H); 7.21 (AA'BB'sy, Δν=12.3 Hz, 4H); 9.50 (d, J=2.91 Hz, 1H).

Minor rotamer (44%)

$^1$H-NMR (300 MHz, CDCl$_3$): δ (ppm): 1.74 (s, 3H); 1.88 (s, 3H); 2.16 (s, 3H); 2.43 (s, 3H); 4.28 (dd, J=6.83 Hz, J=2.93 Hz, 1H); 5.06 (d, J=6.83 Hz, 1H); 7.24 (AA'BB'sy, Δν=19.8 Hz, 4H); 9.61 (d, J=2.93 Hz, 1H).

I.R. (CCl$_4$): 2980 cm$^{-1}$, 1742 cm$^{-1}$, 1732 cm$^{-1}$, 1673 cm$^{-1}$, 1495 cm$^{-1}$, 1395 cm$^{-1}$, 1350 cm$^{-1}$, 1250 cm$^{-1}$.

EXAMPLE 4

Preparation of
(4S,5S)-5-(4-methylthiophenyl)-4-formyl-3-acetyl-2,2-dimethyl-1,3-oxazolidine (Compound 5)

1,4-Diazabicyclooctane (1.44 g; 0.0128 mol) was added to compound 4 (53.7 g; 0.182 mol) kept under mechanical stirring at 30° C. under nitrogen. The mixture was heated to 40° C.

The reaction was monitored by $^1$H-NMR; as soon as the ratio between compounds 4 and 5 was equal to 50:50, the reaction mixture was seeded with crystallized compound 5 (30 mg).

The reaction mixture became heterogeneous due to the precipitation of compound 5.

At the end of the reaction (ratio 5:4=95:5) the suspension was dissolved into methylene chloride (500 ml) and the organic phase was washed with ammonium chloride (2×20 ml). The organic phase was dried over sodium sulphate and evaporated under vacuum. The residue (53.7 g) was used as crude in the following step.

A sample crystallized by a mixture of isopropanol-/isopropyl ether in ratio 20:80 afforded the compound 5.

Major rotamer (93%)

$^1$H-NMR (300 MHz, CDCl$_3$): δ (ppm): 1.73 (s, 3H); 185 (s, 3H); 1.93 (s, 3H); 2.48 (s, 3H); 4.49 (dd, J=2.8 Hz, J=6.4 Hz, 1H); 5.46 (d, J=6.4 Hz, 1H); 7.27 (AA'BB'sy, Δν=22 Hz, 4H); 9.17 (d, J=2.8 Hz, 1H).

Minor rotamer (7%)

$^1$H-NMR (300 MHz, CDCl$_3$): δ (ppm): 1.64 (s, 3H); 1.89 (s, 3H); 2.23 (s, 3H); 2.47 (s, 3H); 5.00 (d, J=7.0 Hz, 1H); 5.36 (d, J=7.0 Hz, 1H); 7.27 (AA'BB'sy, Δν=22 Hz, 4H); 9.06 (s, 1H).

I.R. (KBr): 1735 cm$^{-1}$, 1660 cm$^{-1}$, 1645 cm$^{-1}$.
M.p.=97°-102° C.

EXAMPLE 5

Preparation of
(4R,5S)-5-(4-methylthiophenyl)-4-hydroxymethyl-3-acetyl-2,2-dimethyl-1,3-oxazolidine (Compound 6)

Calcium chloride (14.25 g; 0.13 mol) and sodium borohydride (4.95 g; 0.13 mol) were added to a solution of the crude compound 5 (53.7 g; 0.18 mol) in ethanol (570 ml) and tetrahydrofurane (220 ml kept under mechanical stirring at −5° C. under nitrogen. After 2 hours the reaction was poured into a pH 7 buffered phosphate solution (100 ml) and extracted with methylene chloride (2×300 ml). The collected organic phases were dried over sodium sulphate and evaporated under vacuum to give a residue (44.7 g; 95% compound 6, 5% compound 3) which was crystallized from toluene.

35.0 g of 99% pure compound 6 were obtained.

$^1$H-NMR (300 MHz, DMSO): δ (ppm): 1.58 (s, 3H); 1.62 (s, 3H); 2.10 (s, 3H); 2.46 (s, 3H); 3.03 (ddd, J=11.2 Hz, J=5.1 Hz, J=5.3 Hz, 1H); 3.18 (ddd, J=11.2 Hz, J=8.0 Hz, J=5.3 Hz, 1H); 4.25 (ddd, J=5.0 Hz, J=8.0 Hz, J=5.1 Hz, 1H); 4.65 (t, J=5.3 Hz, 1H); 5.25 (d, J=5.0 Hz, 1H); 7.27 (AA'BB'sy, Δν=30.6 Hz, 4H).

I.R. (KBr): 3320 cm$^{-1}$, 1630 cm$^{-1}$.
M.p.=123°-128° C.

EXAMPLE 6

Preparation of Compound 6 from Compound 5
(alternative method)

Sodium borohydride (32.2 mg; 0.85 mmol) was added to a solution of pure compound 5 (250 mg; 0,85 mmol) in isopropanol (7.7 ml) kept under mechanical stirring at −20° C. under nitrogen. After 2 hours the reaction was poured into a pH 7 buffered phosphate solution (10 ml) and extracted with methylene chloride (2×50 ml). The combined organic phases were dried over sodium sulphate and evaporated under vacuum to give the compound 6 having the same characteristics shown in example 5.

EXAMPLE 7

Preparation of compound 6 from compound 5
(alternative method)

Sodium borohydride (0.52 g, 13.65 mmol) and calcium chloride (1.52 g; 13.65 mmol) were added to a solution of pure compound 5 (4 g; 13.65 mmol) in absolute ethanol (42.7 ml) and tetrahydrofurane (16 ml) kept under stirring at −5° C. under nitrogen. After 20 minutes the reaction was poured into a buffered phosphate solution (10 ml) (KH$_2$PO$_4$/K$_2$HPO$_4$=1:1 mol in 1 l) at pH 7 and extracted with methylene chloride (2×20 ml). The organic phase was dried and the solvent was removed under vacuum up to residue (compound 6 having the same characteristics shown in the example 5).

EXAMPLE 8

Preparation of
(2R,3R)-3-(4-methylthiophenyl)-2-amino-1,3-propanediol [(2R,3R)-thiomicamine]

Monohydrated p-toluenesulphonic acid (20 g; 105 mmol) was added at 25° C. under stirring to a suspension of compound 6 (10.0 g; 33.9 mmol) in water (60 ml).

The suspension was heated to 75° C. for 2.5 hours; the solid dissolved in solution. The solution was heated to 95° C. and kept at this temperature for 42 hours. The solution was then cooled to 15° C. and during the cooling the p-toluenesulphonate of 2R,3R-thiomicamine precipitated.

After 1 hour the solid was filtered at 15° C. and washed with water (20 ml).

Sodium hydroxide (1.2 g) was added to the solid suspended in water (40 ml) at 25° C., up to pH 10.5. From the solution, which was cooled to 5° C., 2R,3R-thiomicamine precipitated and was filtered, washed with water (20 ml) and dried in oven at 60° C. for 4 hours (4.3 g; 97% HPLC titre, 92% diastereomeric excess).

The solid was crystallized from isopropanol (100 ml) at 5° C.

3.4 g of pure 2R,3R-thiomicamine were obtained ($[\alpha]_D^{20} = -33.8°$, 99.8%. HPLC titre, 99% diastereomeric excess).

EXAMPLE 9

Preparation of Compound 3 (see Example 2)—alternative method

A suspension of (2S,3S)-thiomicamine (100 g; 0.469 mol) in toluene (920 ml) and acetone (100 ml) was heated under reflux under stirring for 18 hours in a flask equipped reflux condenser and dean stark trapp; 10.6 g of a mixture containing acetone (3.9 g), water (6.6 g) and toluene (0.1 g) were separated. At the end the solvent was evaporated under vacuum.

(4S,5S)-5-(4-methylthiophenyl)-4-hydroxymethyl-2,2-dimethyl-1,3-oxazolidine (compound 7) (117 g) was obtained which was directly used for the following step.

Compound 7:

$^1$H-NMR (300 MHz, CDCl$_3$): δ (ppm): 1.51 (s, 3H); 1.52 (s, 3H); 2.46 (s, 3H); 3.17 (ddd, J=8.43 Hz, J=4.10 Hz, J=3.48 Hz, 1H); 3.62 (dd, J=4.10 Hz, J=11.1 Hz, 1H); 3.80 (dd, J=3.48 Hz, J=11.1 Hz, 1H); 4.62 (d, J=8.17 Hz, 1H); 7.24 (AA'BB'sy, Δν=21.8 Hz, 4H).

Acetyl chloride (29.4 g; 0.375 mol) was added in 2 hours to a solution of compound 7 (90.38 g; 0.36 mol) in methylene chloride (900 ml) and triethylamine (54.2 g; 0.54 mol) kept under stirring at 15° C. inert atmosphere.

The reaction mixture was then worked up by adding a 10% ammonium chloride solution (200 ml). After separation of the phases, the aqueous phase was extracted with methylene chloride (200 ml). The combined organic phases were dried over sodium sulphate and evaporated to dryness.

Potassium carbonate (24.8 g; 0.18 mol) was added to a solution of the residue in methanol (300 ml) kept under stirring at 25° C.

After 1 hour the solvent was evaporated under vacuum and the residue was dissolved in methylene chloride (300 ml). The solution was washed with water, dried over sodium sulphate and evaporated to dryness. A residue was obtained which, crystallized from ethyl acetate, afforded the pure compound 3 (69 g; 0.234 mol; 65% yield) having the same characteristics shown in the example 2.

EXAMPLE 10

Preparation of
(2S,3S)-3-(4-methylthiophenyl)-3-ethoxy-2-amino-propan-1-ol (Compound 8) and of
(2S,3S)-3-(4-methylthiophenyl)-3-ethoxy-2-acetamido-propan-1-ol (Compound 9)

96% Sulphuric acid (d=1.835) (18.4 g; 10 ml; 187.6 mmol) was added under stirring at room temperature to a suspension of (2S,3S)-thiomicamine (10 g; 46.9 mmol) in ethanol (70 ml).

The mixture was heated to 90° C. for 0.5 hours, cooled to room temperature and poured into a sodium hydroxide solution (15 g; 375 mmol) in water (200 ml) to pH 10–11.

The compound 8 thus obtained was extracted with methylene chloride (2×300 ml), dried over sodium sulphate, evaporated to dryness and used as crude in the following step.

Triethylamine (8.3 g; 82.22 mmol) and acetyl chloride (6.45 g; 82.22 mmol) were added under stirring at room temperature and under nitrogen to a solution of crude compound 8 (18.5 g; 82.22 mmol) in methylene chloride (92.5 ml).

After 15 minutes the reaction was poured into a 10% sodium bicarbonate solution (100 ml). The aqueous phase was extracted with methylene chloride (100 ml); the combined organic phases were dried over sodium sulphate and evaporated to dryness.

The residue (15.62 g) (compound 9) thus obtained was purified by column chromatography (silica gel, eluent: ethyl acetate).

$^1$H-NMR (300 MHz, CDCl$_3$): δ (ppm): 1.19 (t, J=7.0 Hz, 3H); 1.94 (s, 3H); 2.47 (s, 3H); 3.35 (dq, J=9.45 Hz, J=7.0 Hz, 1H); 3.47 (dq, J=9.46 Hz, J=7.0 Hz, 1H); 3.63 (dd, J=12; 5.1 Hz; 1H); 3.65 (dd, J=12.9 Hz; 1H); 4.01 (dddd, J=7.3;9.2;5.1;4.0 Hz; 1H); 4.55 (d, J=4 Hz, 1H); 6.09 (d, J=7.8 Hz, 1H); 7.20 (AA'BB'sy, Δν=20 Hz, 4H).

I.R. (CCl$_4$): 3450 cm$^{-1}$, 2980 cm$^{-1}$, 2930 cm$^{-1}$, 2880 cm$^{-1}$, 1675 cm$^{-1}$, 1495 cm$^{-1}$, 1095 cm$^{-1}$.

EXAMPLE 11

Preparation of
(2R,3S)-3-(4-methylthiophenyl)-3-ethoxy-2-acetamido-1-propanate (Compound 10) and of the (2S,3S) diastereomer thereof (Compound 11)

A solution of dimethylsulphoxide (780 mg; 9.99 mmol) in methylene chloride (1 ml) was added to a solution of oxalyl chloride (475 mg; 3.74 mmol) in methylene chloride (4 ml) kept at −60° C. under nitrogen. After 30 minutes a solution of compound 9 (1.0 g; 3.53 mmol) in methylene chloride (7 ml) was added. The reaction mixture was kept at −60° C. for 30 minutes, then a solution of triethylamine (1.86 g; 18.4 mmol) in methylene chloride (2 ml) was added at −60° C. under stirring.

The reaction mixture was kept at −60° C. for 15 minutes, then was heated to 0° C. in 1 hour and poured into a 5% sodium bicarbonate solution (10 ml). The aqueous phase was washed with methylene chloride (30 ml); the combined organic phases were dried over sodium sulphate and evaporated under vacuum to give an oily residue (505 mg).

The reaction directly afforded an equilibrium mixture of two epimer compounds (Compound 10 and 11).

Major diastereomer:

$^1$H-NMR (300 MHz, CDCl$_3$): δ (ppm): 1.18 (t, J=7.0 Hz, 3H); 1.99 (s, 3H); 2.47 (s, 3H); 3.44 (m, Δν=70 Hz, 2H); 4.75 (dd, J=3.9 Hz, J=7.4 Hz, 1H); 4.95 (d, J=3.9 Hz, 1H); 6.11 (d, J=7.4 Hz, 1H); 7.17 (AA'BB'sy, Δν=32 Hz, 4H); 9.77 (s, 1H).

Minor diastereomer:

$^1$H-NMR (300 MHz, CDCl$_3$): δ (ppm): 1.16 (t, J=7.0 Hz, 3H); 2.06 (s, 3H); 2.50 (s, 3H); 3.44 (m, Δν=70 Hz, 2H); 4.73 (dd, J=3.7 Hz, J=7.4 Hz, 1H); 4.75 (d, J=3.7 Hz, 1H); 6.38 (d, J=7.4 Hz, 1H); 7.32 (AA'BB'sy, Δν=30.9 Hz, 4H); 9.53 (s, 1H).

EXAMPLE 12

Preparation of (2R,3S)-3-(4-methylthiophenyl)-3-ethoxy-2-acetamido-propan-1-ol (Compound 12)

Calcium chloride (24 mg; 0.22 mmol) and sodium borohydride (12.3 mg; 0.33 mmol) were added to a mixture of compounds 10 and 11 (50 mg; 0.0177 mmol) in ethanol (0.34 ml) and tetrahydrofurane (0.22 ml) kept under mechanical stirring at −5° C. under nitrogen. After 2 hours the reaction was poured into a pH 7 buffered phosphate solution (10 ml) and extracted with methylene chloride (2×20 ml). The combined organic phases were dried over sodium sulphate and evaporated under vacuum to give a residue which was crystallized from toluene.

50 mg of a mixture formed by compound 12 and its (2S,3S) diastereomer in ratio 1:1 were obtained.

$^1$H-NMR (300 MHz, CDCl$_3$): δ (ppm): 1.22 (t, J=6.5 Hz, 3H); 2.08 (s, 3H); 2.49 (s, 3H); 3.45 (m, Δν=90 Hz, 2H); 3.87 (dd, J=2.3, J=11.3, 1H); 3.93 (m, Δν=15 Hz, 1H); 4.3 (m, Δν=18 Hz, 1H); 4.71 (d, J=3.1 Hz, 1H); 6.44 (d, J=6.6 Hz, 1H); 7.28 (ABsy, Δν=32 Hz, 4H).

EXAMPLE 13

Preparation of (2R,S,4S,5S)-5-(4-methylthiophenyl)-4-acetoxymethyl-3-acetyl-2-methoxy-1,3-oxazolidine (Compound 13)

Monohydrated paratoluenesulphonic acid (16.2 mg) to a mixture of compound 1 (see Example 1), trimethylorthoformiate (5 ml), heated to 40° C. under stirring.

The reaction mixture was kept under stirring at 40° C. for 1 hour and then poured into 8% NaHCO$_3$ and extracted with CH$_2$Cl$_2$ (2×25 ml). The combined organic phases were dried.

By removing the solvent under vacuum a residue (510 mg) principally formed by compound 13 was obtained.

EXAMPLE 14

Preparation of (2R,S,4S,5S)-5-(4-methylthiophenyl)-4-hydroxymethyl-3-acetyl-2-methoxy-1,3-oxazolidine (Compound 14)

NaOH (1.42 g) was added under stirring at room temperature to a solution of compound 13 (210 mg; 0.65 mol) in CH$_3$OH (3 ml). It was kept under stirring for 30 minutes, poured into water and extracted with methylene chloride (2×25 ml).

By evaporation of the combined organic extracts the compound 14 was obtained.

$^1$H-NMR (300 MHz, CDCl$_3$): δ (ppm): 2.2 (s, 3H); 2.48 (s, 3H); 3.46 (s, 3H); 3.74 (dd, J=6.3 Hz, J=12.0 Hz, 1H); 3.83 (dd, J=2.0 Hz, J=12.0 Hz, 1H); 3.96 (ddd, J=6.3 Hz, J=2.0 Hz, J=8.7 Hz, 1H); 4.92 (d, J=8.7 Hz, 1H); 5.97 (s, 1H); 7.28 (ABsy, Δν=20 Hz, 4H).

EXAMPLE 15

Preparation of (4S,5S)-5-(4-methylthiophenyl)-4-benzoyloxymethyl-3-benzoyl-2,2-dimethyl-1,3-oxazolidine (Compound 15)

Benzoyl chloride (56 g; 0.41 mol) was added without exceeding the temperature of 5° C. to a mixture of compound 7 (see Example 9) (50 g; 0.198 mol) in methylene chloride (250 ml) and triethylamine (42 g; 0.42 mol) cooled to 0° C.

After 1 hour from the end of the addition, the reaction mixture was poured into water (200 ml). The phases were separated and the organic phase was dried over sodium sulphate and evaporated to residue under vacuum. 78 g of compound 15 were obtained.

$^1$H-NMR (300 MHz, DMSO): δ (ppm): 1.7 (s, 6H); 2.49 (s, 3H); 4.00 (2H); 4.29 (1H); 5.12 (d, 1H, J=7.6 Hz); 7.28–7.85 (14H, aromatics).

EXAMPLE 16

Preparation of (4S,5S)-5-(4-methylthiophenyl)-4-hydroxymethyl-3-benzoyl-2,2-dimethyl-1,3-oxazolidine (Compound 16)

A mixture of compound 15 (70 g; 0.15 mol), methanol (500 ml), K$_2$CO$_3$ (22 g; 0.16 mol), was stirred at room temperature for 1 hour. The insoluble salts were filtered and it was evaporated under vacuum to dryness.

The residue was dissolved into methylene chloride (200 ml), the solution was washed with water (2×100 ml). The organic phase was dried over sodium sulphate and the solvent was evaporated under vacuum to give a residue (55 g) principally formed by compound 16.

$^1$H-NMR (300 MHz, DMSO): δ (ppm): 1.68 (s, 6H); 2.49 (s, 3H); 3.00 (2H); 3.82 (1H); 5.07 (d, 1H, J=7.6 Hz); 7.27–7.5 (9H, aromatics).

By column chromatography on silica gel (eluent ethyl ether) of a sample the pure product was obtained with m.p.=128°–131° C.

EXAMPLE 17

Preparation of (4R,5S)-5-(4-methylthiophenyl)-4-formyl-3-benzoyl-2,2-dimethyl-1,3-oxazolidine (Compound 17)

A solution of DMSO (780 mg; 10 mmol) in CH$_2$Cl$_2$ (10 ml) was added under stirring and under nitrogen to a solution of oxalyl chloride (470 mg; 3.70 mmol) in CH$_2$Cl$_2$ (2 ml) cooled to −60° C.

The solution was stirred at −60° C. for 30 minutes. A solution of compound 16 (1.25 g; 3.5 mmol) in methylene chloride (8 ml) was added in 15 minutes to the solution kept at −60° C. under stirring. The mixture was kept under stirring at −60° C. for 15 minutes and then Et$_3$N (2.1 g; 2 ml) in methylene chloride (2 ml) was added to the solution.

The solution temperature was heated to 0° C. and the solution was poured into water (50 ml); the phases were separated and the organic phase, after drying over sodium sulphate, was evaporated under vacuum to give a residue (1.35 g) formed by compound 17.

$^1$H-NMR (300 MHz, DMSO): δ (ppm): 1.75 (6H); 2.48 (s, 3H); 4.47 (dd, 1H, J=8.3 Hz, J=3.5 Hz); 5.19 (d, 1H, J=8.3 Hz); 7.27–7.51 (9H, aromatics); 9.14 (d, 1H, J=3.5 Hz).

EXAMPLE 18

Preparation of (4S,5S)-5-(4-methylthiophenyl)-4-methylsulphonyloxymethyl-3-benzoyl-2,2-dimethyl-1,3-oxazolidine (Compound 18)

Mesyl chloride (630 mg; 5.5 mmol) was added under stirring and under nitrogen at 0° C. to a solution of compound 16 (see Example 16) (1.5 g; 9.2 mmol), Et$_3$N (600 mg; 6 mmol) in CH$_2$Cl$_2$ (7.5 ml).

The mixture was stirred at 0° C. for 1 hour, then poured into water (20 ml). The organic phase was dried over Na$_2$SO$_4$ and the solvent was evaporated under vacuum to give a residue which was chromatographed on SiO$_2$ with Et$_2$O to afford the compound 18 (800 mg).

$^1$H-NMR (300 MHz, DMSO): δ (ppm): 1.66 (s, 6H); 2.49 (s, 3H); 3.13 (s, 3H); 3.95 (m, 2H); 4.18 (ddd, 1H, J=7.6 Hz, J=3.91 Hz, J=2.63 Hz); 5.04 (d, 1H, J=7.6 Hz); 7.30–7.55 (5H, aromatics).

EXAMPLE 19

Preparation of (2S,3R)-3-(4-methylthiophenyl)-2-acetamido-1,3-propanediol (Compound 19)

(2S,3S)-Thiomicamine (30 g; 0.141 mol) in acetic acid (130 ml) was heated under reflux (117° C.) for 23 hours.

Evaporation of the solvent under vacuum afforded a residue which was dissolved into methanol (130 ml). Sodium hydroxide (14.6 g; 0.36 mol) was added at 15° C. to the thus obtained solution.

The reaction mixture was brought to pH 6.2 with hydrochloric acid and evaporated under vacuum.

The oily residue was dissolved into methylene chloride (80 ml) and water (100 ml).

After separation of the phases, the organic phase was dried over sodium sulphate and evaporated to dryness.

The compound 19 (3.4 g; diastereomeric ratio 98:2) was obtained by crystallization from ethyl acetate.

$^1$H-NMR (300 MHz, CDCl$_3$): δ (ppm): 1.73 (s, 3H); 2.47 (s, 3H); 3.63 (dd, J=7.5 Hz, J=3.5 Hz, 1H); 3.84 (dd, J=7.5 Hz, J=2.9 Hz, 1H); 4.06 (dddd, J=2.9 Hz, J=3.5 Hz, J=4.0 Hz, J=7.8 Hz, 1H); 7.30 (ABsy, Δν=30 Hz).

300 mg of pure compound 19 were reflux heated for 5 hours with NaOH. By saturating the solution with NaCl (2S,3R)-thiomicamine precipitated.

[α]$_D^{25}$= −26.44°

EXAMPLE 20

Preparation of (4S,5S)-5-(4-methylthiophenyl)-4-formyl-3-acetyl-2,2-dimethyl-1,3-oxazolidine (Compound 5)

Pyrrolidine (9.6 mg; 0.065 mmol) was added at 25° C. to a solution of compound 4 (see example 3) (100 mg, 0.34 mmol) in toluene (2 ml) kept under magnetic stirring and under nitrogen. At the end of the addition the mixture was kept at 25° C. under stirring for 14 hours. The reaction mixture was then poured into 10% NaHCO$_3$; after separation of the phases, the aqueous phase was extracted with CH$_2$Cl$_2$. The combined organic phases were dried over sodium sulphate and evaporated to dryness under vacuum.

A mixture of compound 4 and compound 5 in the ratio 38:62 was obtained.

EXAMPLE 21

Preparation of (4S,5S)-5-(4-methylthiophenyl)-4-hydroxymethyl-1,3-oxazolidine (Compound 20)

Paraformaldehyde (1.48 g; 49.84 mmol) was added to a suspension of (2S,3S)-thiomicamine (10 g; 46.9 mmol) in toluene (60 ml).

The mixture was heated at reflux under magnetic stirring for 1.5 hours while distilling through a dean stark trapp.

The reaction mixture was cooled down and toluene was evaporated under vacuum up to an oily residue which was used without any purification in the next reactions.

EXAMPLE 22

Preparation of (4S,5S)-5-(4-methylthiophenyl)-4-hydroxymethyl-3-acetyl-1,3-oxazolidine (Compound 21)

Triethylamine (560 mg; 5.55 mmol) and thereafter acetyl chloride (309 mg; 3.93 mmol) were added to a solution of compound 20 (1 g; 3.7 mmol) in methylene chloride (10 ml).

After 1 hour a 10% sodium bicarbonate aqueous solution was added to the reaction mixture; the phases were separated and the organic one was washed with a buffered phosphate solution having pH 7. The organic extract was dried over sodium sulphate and evaporated to dryness.

The crude thus obtained was chromatographed on silica gel using a mixture of diethylether and ethylacetate.

Compound 21 was obtained pure in the form of two conformers (rotamers).

Major rotamer:
$^1$H-NMR (300 MHz, CDCl$_3$): δ (ppm): 1.98 (s, 3H); 2.47 (s, 3H); 3.59 (m, Δν=30 Hz, 2H); 3.86 (ddd, J=5.1 Hz, 5 Hz, 5 Hz, 1H); 4.94 (d, J=4.2 Hz, 1H); 5.08 (d, J=5.1 Hz, 1H); 5.27 (d, J=4.2 Hz, 1H); 7.20–7.32 (aromatic protons, 4H).

Minor rotamer:
$^1$H-NMR (300 MHz, CDCl$_3$): δ (ppm): 2.00 (s, 3H); 2.47 (s, 3H); 3.59 (m, Δν=30 Hz, 2H); 3.93 (ddd, J=3.6 Hz; J=5.81; J=5.81 Hz, 2H); 4.75 (d, J=5.1 Hz, 1H); 5.08 (d, J=3.6 Hz, 1H); 5.30 (d, J=5.1 Hz, 1H); 7.20–7.32 (aromatic protons, 4H).

EXAMPLE 23

Preparation of Compound 6 from Compound 5 (alternative method)

Compound 5 (500 mg) was added to a solution of acetic acid (24 mg) in ethanol (10 ml).

Sodium borohydride (16 mg) was added under stirring to the solution cooled to −5° C.

The solution was kept under stirring for 1 hour and then poured into a pH 7 buffered aqueous solution and extracted with methylene chloride (2×25 ml).

The combined organic phases were washed with water and the solvent was evaporated under vacuum to give compound 6 (500 mg) having the same characteristics shown in example 5.

EXAMPLE 24

Preparation of
(2S,3S)-3-(4-methylthiophenyl)-3-methoxy-2-aminopropan-1-ol (Compound 22) and of
(2S,3S)-3-(4-methylthiophenyl)-3-methoxy-2-acetamido-propan-1-ol (Compound 23)

96% Sulphoric acid (d=1.835) (1.84 g; 1 ml; 18.77 mmol) was added at room temperature under stirring to a suspension of (2S,3S)-thiomicamine (1 g; 4.69 mmol) in methanol (4.9 ml).

The mixture was heated at 90° C. for 0.5 hours, cooled to room temperature and poured into a solution of sodium hydroxide (1.5 g; 37.5 mmol) in water (15 ml) to a pH of 10–11.

The (2S,3S)-3-(4-methylthiophenyl)-3-methoxy-2-amino-propan-1-ol (compound 22) thus obtained was extracted with methylene chloride (2×30 ml), dried over sodium sulphate, evaporated to dryness and used in the following step.

$^1$H-NMR (300 MHz, CDCl$_3$): δ (ppm): 2.47 (s, 3H); 2.83 (m, Δν=30 Hz, 1H); 3.2 (s, 3H); 3.3 (dd, J=5.8 Hz, J=10.0 Hz, 1H); 3.42 (dd, J=10.0 Hz, J=3.6 Hz, 1H); 4.02 (d, J=6.9 Hz, 1H); 7.23 (ABsy, Δν=45 Hz, 4H).

Triethylamine (2.6 g; 26.43 mmol) and acetyl chloride (1.52 g; 19.4 mmol) were added to a solution of crude compound 22 (2.0 g; 8.81 mmol) in methylene chloride (10 ml), under stirring at room temperature and under nitrogen.

After 15 minutes the reaction was poured into a 10% sodium bicarbonate aqueous solution (10 ml). The aqueous phase was extracted with methylene chloride (10 ml); the combined organic phases were dried over sodium sulphate and evaporated to dryness.

A residue (compound 23) was obtained, which was crystallized from methylene chloride.

$^1$H-NMR (300 MHz, DMSO): δ (ppm): 1.76 (s, 3H); 2.43 (s, 3H); 3.11 (s, 3H); 3.17 (m, Δν=30 Hz, 1H); 3.43 (m, Δν=30 Hz, 1H); 3.87 (m, Δν=30 Hz, 1H); 4.34 (d, J=4.60 Hz, 1H); 4.77 (t, J=6 Hz, 1H); 7.22 (ABsy, Δν=20 Hz, 4H); 7.68 (d, J=10 Hz, 1H).

EXAMPLE 25

Preparation of
(2R,3S)-3-(4-methylthiophenyl)-3-methoxy-2-acetamido-1-propanale (Compound 24)

A solution of dimethylsulphoxide (64 mg; 0.82 mmol) in methylene chloride (0.1 ml) was added to a solution of oxalyl chloride (40 mg; 0.32 mmol) in methylene chloride (300 μl) kept at −60° C. under nitrogen. After 30 minutes a solution of compound 23 (80 mg; 3.53 mmol) in methylene chloride was added. The reaction mixture was kept at −60° C. for 30 minutes, then a solution of triethylamine (211 mg; 2 mmol) in methylene chloride (2 ml) was added at 60° C. under stirring. The reaction mixture was kept at −60° C. for 15 minutes, then was heated to 0° C. in 1 hours and poured into a 5% sodium bicarbonate aqueous solution (20 ml). The aqueous phase was washed with methylene chloride (30 ml); the combined organic phases were dried over sodium sulphate and evaporated under vacuum to give an oily residue (85 mg) (Compound 24).

$^1$H-NMR (300 MHz, DMSO): δ (ppm): 1.81 (s, 3H); 2.43 (s, 3H); 3.10 (s, 3H); 4.58 (dd, J=3.7 Hz, J=8.10 Hz, 1H); 4.92 (d, J=3.7 Hz, 1H); 7.24 (ABsy, Δν=45 Hz, 4H); 8.22 (d, J=8.5 Hz, 1H); 9.56 (s, 1H).

EXAMPLE 26

Preparation of
(4S,5S)-5-(4-methylthiophenyl)-4-hydroxymethyl-2,2-diethyl-1,3-oxazolidine (Compound 25)

By working as described in the example 9 and using 3-pentanone (100 ml) instead of acetone the compound 25 was obtained in quantitative yield.

$^1$H-NMR (300 MHz, CDCl$_3$): δ (ppm): 0.98 (t, J=7.5 Hz, 3H); 1.04 (t, J=7.5 Hz, 3H); 1.76 (q, J=7.5 Hz, 2H); 1.80 (q, J=7.5 Hz, 2H); 2.47 (s, 3H); 3.17 (dd, J=8.8; 4.0; 3.5 Hz, 1H); 3.63 (dd, J=4.0; 11.3 Hz, 1H); 3.82 (dd, J=3.5; 11.3 Hz, 1H); 4.62 (d, J=8.8 Hz, 1H); 7.20–7.34 (aromatics, 4H).

I.R. (film): 2970 cm$^{-1}$, 2920 cm$^{-1}$, 1600 cm$^{-1}$, 1500 cm$^{-1}$, 1205 cm$^{-1}$, 1090 cm$^{-1}$, 1060 cm$^{-1}$.

EXAMPLE 27

Preparation of compound 4 (see Example 3)—alternative method

Dimethylsulphoxide (0.78 g; 10 mmol) was added under nitrogen to a mixture of compound 3 (example 2) (1.18 g; 4 mmol) in methylene chloride (7.5 ml).

It was cooled to −15° C. and phosphoric anhydride (1.42 g; 10 mmol) was added to it.

The solution was kept at −15° C. under stirring for 0.5 hours. Triethylamine (2 g; 20 mmol) was slowly added dropwise. After 10 minutes from the end of the addition, the mixture was poured into water (50 ml); the phases were separated.

The organic phase was washed with a sodium chloride saturated solution (50 ml), dried over sodium sulphate, evaporated to residue to give 1.35 g of a crude which was almost exclusively formed by the desired product (compound 4).

EXAMPLE 28

Preparation of compound 4 (see Example 3)—alternative method

Pyridine (1.6 g; 20 mmol) was added under nitrogen to a mixture of compound 3 (example 2) (1.18 g; 4 mmol) in methylene chloride (10 ml).

A solution of chlorine (4 mmol) in carbon tetrachloride was added at room temperature to the previous solution.

It was kept at room temperature under stirring for 0.5 hours.

The reaction mixture was poured into water (50 ml); the phases were separated.

The organic phase was washed with 4N hydrochloric acid. The solution was dried over sodium sulphate and evaporated to residue to give 1.36 g of a crude which was formed by the desired product (compound 4).

EXAMPLE 29

Preparation of compound 4 (see Example 3)—alternative method

A mixture of chronic anhydride (2.1 g), pyridine (3.2 g) and methylene chloride (50 ml) was added, at room temperature, under nitrogen, to a solution of compound 3 (example 2) (1 g) in methylene chloride (15 ml).

It was kept at room temperature under stirring for 15 minutes.

The solution was decanted and the residue was washed with ethyl ether (2×30 ml). The combined organic phases were evaporated to residue. The residue was dissolved in methylene chloride (50 ml) and the solution was washed with diluted hydrochloric acid.

The organic phase was washed with a sodium chloride saturated solution (50 ml), dried over sodium sulphate, evaporated to residue to give 0.8 g of a crude containing the desired product (compound 4).

EXAMPLE 30

Preparation of compound 4 (see Example 3)—alternative method

A solution prepared by dissolving compound 3 (example 2) (2.36 g; 8 mmol) and triethylamine (0.8 g; 8 mmol) in methylene chloride (15 ml) was added in 20 minutes, under stirring, to a solution of dimethylsulphide (0.62 g; 10 mmol) and chlorine (0.71 g; 10 mmol) cooled to $-20°$ C.

It was kept at $-20°$ C. under stirring for 0.5 hours. Triethylamine (2 g; 20 mmol) was added dropwise. After 10 minutes from the end of the addition, the reaction mixture was poured into water (50 ml); the phases were separated.

The organic phase was washed with a sodium chloride saturated solution (50 ml), dried over sodium sulphate, evaporated to residue to give 2.40 g of a crude which was formed by the desired product (compound 4).

EXAMPLE 31

Preparation of compound 4 (see Example 3) from compound 3 (see Example 2)

A) Chlorine (2.35 g; 33.1 mmol) was added under stirring to a mixture of dimethylsulphide (2.17 g; 35 mmol) in methylene chloride (25 ml) cooled to $-30°$ C. A solution of triethylamine (3 g; 30 mmol) and compound 3 (8.85 g; 30 mmol) in methylene chloride (70 ml) was added dropwise to the mixture kept at $-20°$ C. A solution of triethylamine (7.6 g; 75 mmol) in methylene chloride (20 ml) was added dropwise in 30 minutes under stirring to the reaction mixture kept at $-20°$ C. At the end of the addition the reaction mixture was heated to $0°$ C. and poured into water (150 ml). After separation of the phases the organic phase was dried over sodium sulphate and evaporated under vacuum to give an oily residue (9 g) containing 4.6 g of 4.

B) Trichlorocyanuric acid (4.6 g; 20 mmol) was added portionwise under stirring to a mixture of compound 3 (5.9 g; 20 mmol) and pyridine (7.9 g; 100 mmol) in methylene chloride (50 ml) cooled to $0°$ C. The mixture was kept under stirring at $0°$ C. for 1 hour and then poured into water (150 ml). The organic phase was washed with 1N hydrochloric acid (120 ml) and dried over sodium sulphate. The solvent was evaporated under vacuum to give 6 g of a residue containing 4.

C) Trichlorocyanuric acid (2.32 g; 10 mmol) was added portionwise to a mixture of compound 3 (2.95 g; 10 mmol) and dimethylsulphide (0.68 g; 11 mmol) in methylene chloride (29.5 ml) cooled to $-20°$ C. Triethylamine (4.05 g; 40 mmol) was added dropwise under stirring to the mixture kept at $-20°$ C. for 0.5 hours. At the end of the addition the mixture was poured into water (100 ml); after separation of the phases, the organic phase was washed with 0.1N hydrochloric acid (50 ml) and dried over sodium sulphate.

3.9 g of a residue containing 4 were obtained.

D) Phosphoric anhydride (2.85 g; 20 mmol) was added portionwise under stirring to a mixture of dimethylsulphoxide (2.34 g; 30 mmol), dimethylformamide (6 ml) and compound 3 (2.95 g; 10 mmol) cooled to $15°$ C., while the reaction mixture spontaneously warmed up to $50°$ C. The mixture was stirred for 2 hours at $50°$ C., cooled to $20°$ C. and poured into a mixture of water (50 ml) and methylene chloride (50 ml).

After separation of the phases the organic phase was dried over sodium sulphate and evaporated to residue under vacuum. 4.5 g of a residue containing 2.1 g of 4 were obtained.

E) Phosphoric anhydride (4.3 g; 30 mmol) was added, portionwise and by keeping the temperature between $0°$ and $5°$ C., to a mixture of dimethylsulphoxide (11 g; 0.14 mol) and methylene chloride (6 ml).

Compound 3 (5.9 g; 20 mmol) was added portionwise under stirring in 30 minutes to the mixture kept at $0°$ C. and after further 30 minutes, triethylamine (4.1 g; 40 mmol) was added in 1 hour.

The reaction mixture was poured into a mixture of water (50 ml) and methylene chloride (50 ml). After separation of the phases the organic phase was dried over sodium sulphate and removed up to residue under vacuum. 6.5 g of a residue containing 4 g of compound 4 were obtained.

F) Phosphoric anhydride (17 g; 0.12 mol) was added under stirring to a solution of dimethylsulphoxide (13.2 g; 0.169 mol), dimethylformamide (25 g) in methylene chloride (100 ml) cooled to $0°$ C. and after 30 minutes compound 3 (17.5 g; 0.059 mol). Triethylamine (18 g; 0.18 mol) was added in 1 hour under stirring to the mixture while keeping the temperature between $0°$ C. and $5°$ C.

The mixture was poured into water (100 ml) and the organic phase was dried over sodium sulphate and evaporated to dryness under vacuum. 34.5 g of a residue containing 15 g of compound 4 were obtained.

G) Trichlorocyanuric acid (2.32 g; 10 mmol) was added portionwise under stirring to a mixture of compound 3 (2.95 g; 10 mmol) in methylene chloride (29.5 ml) and methyl-phenyl-thioether (1.37 g; 11 mmol) cooled to $-20°$ C. Triethylamine (4.05 g; 40 mmol) was added dropwise under stirring to the mixture kept at $-20°$ C. for 0.5 hours. At the end of the addition the mixture was poured into water (100 ml) and after separation of the phases the organic phase was washed with 0.1N hydrochloric acid (50 ml), dried over sodium sulphate and evaporated under vacuum.

4.1 g of a crude containing compound 4 were obtained.

H) Trichlorocyanuric acid (2.32 g; 10 mmol) was added portionwise under stirring to a solution of compound 3 (2.95 g; 10 mmol) in methylene chloride (29.5 ml) cooled to $-20°$ C. Triethylamine (4.05 g; 40 mmol) was added dropwise to the mixture kept under stirring at $-20°$ C. for 0.5 hours. The mixture was poured into water (100 ml) and after separation of the phases the organic phase was dried over sodium sulphate and evaporated under vacuum.

3 g of a crude containing 600 mg of compound 4 were obtained.

I) Phosphoric anhydride (4.25 g; 30 mmol) was added portionwise, keeping the temperature between $0°$ and $5°$ C., to a solution of dimethylsulphoxide (2.34 g; 30 mmol), methylene chloride (21 ml), compound 3 (2.95 g; 10 mmol) and triethylamine (1 g; 10 mmol) cooled to $0°$ C. The mixture was kept under stirring for 0.5 hours at $0°$ C. and then triethylamine (3.6 g; 35 mmol) was added dropwise. After 1 hour from the end of the addition the reaction mixture was poured into water (50 ml). After separation of the phases the organic phase was dried over sodium sulphate and evaporated to residue under vacuum.

3 g of a crude containing 2.4 g of the compound 4 were obtained.

J) N-chlorosuccinimide (0.4 g; 3 mmol) was added portionwise to a solution of compound 3 (0.59 g; 2 mmol), dimethylsulphide (0.25 g; 4 mmol) in methylene chloride (6 ml) cooled to −25° C. and kept under nitrogen. Triethylamine (0.3 g; 3 mmol) was added dropwise to the reaction mixture kept at −20° C. for 30 minutes. At the end of the addition the mixture was heated to 0° C. and poured into water (10 ml). The phases were separated and the organic phase was dried over sodium sulphate and evaporated to residue under vacuum.

0.6 g of a crude containing 4 were obtained.

K) 1-Oxo-2,2,6,6-tetramethylpiperidinium chloride, prepared according to the method reported on J. Org. Chem., 53, 1278, (1988) (0.2 g; 1.04 mmol), was added to a solution of compound 3 (0.148 g; 0.502 mmol) and 2,6-lutidine (0.25 ml; 2.1 mmol) in methylene chloride (4 ml) kept between 0° and 5° C. The reaction mixture was kept between 0° and 5° C. under stirring for 30 minutes. The solution was then washed with 0.1N hydrochloric acid, with a 5% sodium bicarbonate aqueous solution and then with water; after separation of the phases the organic phase was dried over sodium sulphate and evaporated to dryness under vacuum to give a residue (250 mg). The product was purified by column chromatography (silica gel, eluent ethyl ether/ethyl acetate) to give the pure 4 (0.11 g).

L) Molecular sieves 4 A (8 g) were added to a solution of compound 3 (4.4 g; 15 mmol) and N-methylmorfoline-N-oxide (3.0 g; 22.5 mmol) in methylene chloride (50 ml) kept under stirring under nitrogen. After 10 minutes tetrapropylammonium perruthenate (0.262 g; 0.75 mmol) was added to the solution. The reaction mixture was kept at 25° C. for 2 hours. After separation of the molecular sieves by filtration, the reaction mixture was washed with 0.1N hydrochloric acid, with a 5% sodium bicarbonate aqueous solution and with water and then dried over sodium sulphate. By evaporation of the solvent under vacuum a residue (4.2 g) was obtained which after chromatography on silica gel (eluent ethyl acetate) afforded the pure compound 4 (2.1 g; 7.2 mmol).

EXAMPLE 32

Preparation of compound 5 (see Example 4) from compound 4 (see Example 3)

A) 1,4-Diazabicyclo-[2,2,2]-octane (300 mg; 2.66 mmol) was added at 45° C. under stirring to a solution of 4 (5 g; 16.9 mmol), n-propylpropionate (2 ml) and diisopropylether (6 ml). After 4 hours (ratio 5:4=60:40 as determined by HPLC of the solution) the solution was cooled to 40° C. and added with compound 5 (100 mg). The reaction temperature was slowly cooled at 20° C. and kept at 20° C. for 15 hours. The suspension was then filtered and the solid was washed with diisopropyl ether (2×2 ml).

After drying, 4 g of a mixture of 5 and 4 in ratio 97:3 were obtained.

Compound 4 (4.2 g) and n-propylpropionate (0.5 g) were added to a solution obtained by combining the filtrate and the isopropyl ether coming from washings (4 ml). The mixture was kept at 40°–45° C. for 3 hours, then cooled to 40° C. and added with compound 5 (100 mg). The reaction mixture was then slowly cooled to 20° C. and kept under stirring at 20° C. for 15 hours. The suspension was then filtered and the solid was washed with diisopropylether (2×2 ml).

4.8 g of 5 and 4 in the ratio 95:5 were obtained.

B) 1,4-Diazabicyclo-[2,2,2]-octane (300 mg; 2.66 mmol) was added at 45° C. under stirring to a solution of 4 (5 g; 16.9 mmol), isoamyl acetate (2 ml) and decahydronaphthalene (6 ml). After 4 hours (ratio 5:4=60:40 as determined by HPLC in the solution) the solution was cooled to 40° C. and added with compound 5 (100 mg). The reaction temperature was slowly cooled to 20° C. and kept at 20° C. for 15 hours. The suspension was then filtered and the solid was washed with decahydronaphthalene (2×2 ml).

After drying, 4 g of a mixture of 5 and 4 in the ratio 97:3 were obtained.

Compound 4 (4.2 g) and isoamyl acetate (0.5 g) were added to a solution obtained by the combining filtrate and the decahydronaphthalene washings (4 ml). The mixture was kept at 40°–45° C. for 3 hours, then cooled to 40° C. and added with compound 5 (100 mg). The reaction mixture was then slowly cooled to 20° C. and kept under stirring at 20° C. for 15 hours. The suspension was then filtered and the solid was washed with decahydronaphthalene (2×2 ml).

4.8 g of 5 and 4 in the ratio 95:5 were obtained.

C) 1,4-Diazabicyclo-[2,2,2]-octane (0.6 g; 0.0053 mol) was added to the compound 4 (15 g; 0.5 mol) kept under stirring at 25° C. The reaction mixture was heated to 45° C. for 3 hours, then isoamyl acetate (9 ml) and diisopropylether (10 ml) were added and the mixture was left to cool spontaneously under stirring up to 25° C. After 1 hour isopropylether (5 ml) was added and the mixture was cooled to 5° C. in 0.5 hours. It was kept at 5° C. for 0.5 hours. The suspension was filtered, washed with isopropylether (2×10 ml) to give 9.0 g of a solid formed by 5 and 4 in the ratio 98:2.

D) 1,4-Diazabicyclooctane (2.5 g; 0.022 mol) was added to compound 4 (60 g; 0.2 mol) kept under stirring at 25° C. Cyclohexane (120 ml) was added to the reaction mixture heated to 50° C. for 2 hours; the reaction was kept at 50° C. for further 2 hours and then cooled to 25° C. After 16 hours the reaction mixture was filtered; a mixture (55 g) of compounds 5 and 4 in the ratio 94:6 was obtained.

E) 1,4-Diazabicyclo-[2,2,2]-octane (300 mg; 2.66 mmol) was added at 45° C. under stirring to a solution of compound 4 (5 g; 16.9 mmol) and propylpropionate (2.5 ml) in methylcyclohexane (6 ml). After 5 hours, the solution was heated to 40° C. and added with compound 5 (100 mg) and with propylpropionate (0.5 ml). The reaction temperature was slowly cooled to 20° C. and kept at 20° C. under stirring for 15 hours. The suspension was filtered and the solid was washed with methylcyclohexane (2×2 ml). The solid (3.5 g) formed by 5 and 4 in ratio 96:4 was obtained.

EXAMPLE 33

Preparation of compound 6 (see example 5) from compound 5 (see example 4)

Compound 5 (245 g; 0.83 mol) was added to a solution of boric acid (21.5 g; 0.35 mol) in ethanol (2100 g). The solution was cooled to 0° C. and added with sodium borohydride (13.2 g; 0.35 mol). The solution was kept under stirring for 2 hours and then poured into a pH 7 buffered aqueous solution and extracted with methylene chloride (2×500 g). The combined organic phases were washed with water and the solvent was evaporated under vacuum to give compound 6 (257 g).

EXAMPLE 34

Preparation of (4R,5S)-5-(4-methylthiophenyl)-4-acetoxymethyl-3-acetyl-2,2-dimethyl-1,3-oxazolidine (compound 26)

Acetyl chloride (3.2 g; 40.8 mmol) was added under stirring at 15° C. to a solution of compound 6 (see example 5) (10 g; 33.9 mmol) and triethylamine (4.2 g; 41.6 mmol) in methylene chloride (60 ml). After 1 hour the reaction was poured into water (50 ml), after separation of the phases, the aqueous phase was extracted with methylene chloride (100 ml) and the combined organic phases were dried over sodium sulphate and evaporated under vacuum. The crude compound 26 was thus obtained which was directly used in the next step (example 35).

EXAMPLE 35

Preparation of (2R,3R)-3-(4-methylthiophenyl)-2-amino-1,3-propanediol [(2R,3R)-Thiomicamine]

Compound 26 (see example 34) (1.1 g; 3.30 mmol) was added at 35° C. under stirring and under nitrogen to a solution of methanesulphonic acid (0.36 g; 3.75 mmol) in methylene chloride (4 ml) and acetic anhydride (0.11 g; 1 mmol). After 30 hours the reaction mixture was added dropwise to a sodium hydroxide solution (1.5 g; 37.5 mmol) in water (4 ml) kept at 20° C. At the end of the addition the mixture was heated to 95° C. for 4 hours. HPLC analysis of the aqueous solution showed the presence of Thiomicamine (0.63 g; 2.97 mmol, 95% yield) with (2R,3R):(2R,3S)=89:11 diastereomeric ratio. The product, which crystallized by cooling the solution, was filtered at 5° C. and washed with water (20 ml). After drying under vacuum the pure (2R,3R)-Thiomicamine (0.61 g; 2.88 mmol; 85% yield) was obtained.

EXAMPLE 36

Preparation of (2R,3R)-Thiomicamine from compound 6 (see example 5)

A) Compound 6 (5.0 g; 16.9 mmol) was added at 15° C. under stirring and under nitrogen to a solution of monohydrated p-toluenesulphonic acid (3.90 g; 20.5 mmol) in acetic anhydride (5.50 g; 53.9 mmol). The reaction was then heated to 35° C. for 8 hours. At the end the solution was cooled to 15° C. and added dropwise to a sodium hydroxide solution (7.5 g; 187 mmol) in water (20 ml). The mixture was then heated to 95° C. for 4 hours under stirring and then cooled to 15° C. in 2 hours. The precipitate thus formed was filtered, washed with water (20 ml) and dried under vacuum at 60° C. to give pure (2R,3R)-Thiomicamine (3.07 g; 14.4 mmol; 84.3% yield).

B) The experiment was carried out following the same procedure described at point A but using monohydrated p-toluenesulphonic acid (0.78 g; 4.1 mmol), acetic anhydride (1.05 g; 10.3 mmol), methylene chloride (4 ml) and compound 6 (1 g; 3.39 mmol). After treatment with sodium hydroxide (1.5 g of NaOH and 4 ml of water) according to the procedure described at point A, Thiomicamine having the ratio (2R,3R):(2R,3S)=90:10 was obtained.

C) The experiment was carried out following the same procedure described at point A but using methanesulphonic acid (0.39 g; 4.1 mmol), acetic anhydride (0.64 g; 6.2 mmol), acetic acid (0.49 g; 8.2 mmol) and compound 6 (1 g; 3.39 mmol). After treatment with sodium hydroxide (1.5 g of NaOH and 4 ml of water) according to the procedure described at point A, Thiomicamine having the ratio (2R,3R):(2R,3S)=92.5:7.5 was obtained.

D) The experiment was carried out following the same procedure described at point A but using monohydrated p-toluenesulphonic acid (0.39 g; 2.05 mmol), acetic anhydride (0.21 g; 2.0 mmol), formic acid (2 g) and compound 6 (0.5 g; 1.69 mmol). After treatment with sodium hydroxide (1.5 g of NaOH and 4 ml of water) according to the procedure described at point A, Thiomicamine having the ratio (2R,3R):(2R,3S)=88:12 was obtained.

EXAMPLE 37

Preparation of (2R,3R)-Thiomicamine

By mild hydrolysis under controlled conditions of compound 6 (see example 5) (2R,3S)-3-(4-methylthiophenyl)-2-acetamido-1,3-propanediol (Compound 27) was obtained from which (2R,3R)-Thiomicamine was prepared according the following procedures:

A) Compound 27 (1.0 g; 3.92 mmol) was added at 15° C. under stirring and under nitrogen to a solution of monohydrated p-toluenesulphonic acid (1.1 g; 5.78 mmol) in acetic anhydride (1.03 g; 9.98 mmol) and methylene chloride (8 ml). The reaction was heated to 25° C. for 16 hours. At the end the solution was cooled to 15° C. and added dropwise to a sodium hydroxide solution (1.4 g; 35 mmol) in water (3 ml). The mixture was then heated to 95° C. for 5 hours.

HPLC analysis of the aqueous solution showed the presence of Thiomicamine with diastereomeric ratio (2R,3R):(2R,3S)=84:16.

B) Compound 27 (1.0 g; 3.92 mmol) was added at 15° C. under stirring and under nitrogen to a solution of monohydrated p-toluenesulphonic acid (1.1 g; 5.78 mmol) in acetic anhydride (1.1 g; 10.78 mmol) and acetic acid (8 ml). The reaction was kept at 25° C. for 35 hours.

The solvent was removed under vacuum at 40° C. and the residue was added to a sodium hydroxide solution (1 g; 25 mmol) in water (4 ml). The mixture was then heated to 95° C. for 5 hours.

HPLC analysis of the aqueous solution showed the presence of Thiomicamine with diastereomeric ratio (2R,3R):(2R,3S)=85:15.

EXAMPLE 38

Preparation of (4S,5S)-5-(4-methylthiophenyl)-4-hydroxymethyl-3-propionyl-2,2-dimethyl-1,3-oxazolidine (compound 28)

Propionyl chloride (2.2 g; 23.6 mmol) was added in 2 hours to a solution of compound 7 (see Example 9) (5 g; 19.7 mmol) and triethylamine (2.4 g; 23.6 mmol) in methylene chloride (70 ml) kept under stirring under nitrogen at 15° C. A 10% ammonium chloride aqueous solution (200 ml) was then added to the reaction mixture. After separation of the phases the aqueous phase was extracted with methylene chloride (100 ml).

The combined organic phases were dried over sodium sulphate and evaporated to dryness. A residue was obtained which after crystallization from ethyl acetate afforded the pure compound 28 (4.6 g; 15 mmol, 77% yield) having the following characteristics:

$^1$H-NMR (300 MHz, 80° C. in DMSO-d$_6$): δ (ppm): 0.99 (t, J=7.3 Hz, 3H), 1.45 (s, 3H); 1.5 (s, 3H); 2.37 (q, J=7.3 Hz, 2H); 2.47 (s, 3H); 3.58 (ddd, J=11.23 Hz, J=6.59 Hz, J=4.15 Hz, 1H); 4.08 (ddd, J=3.9 Hz, J=4.15 Hz, J=6.59 Hz, 1H); 5.07 (d, J=3.9 Hz, 1H); 7.31 (AA'BB' system, Δν=42 Hz, 4H).

EXAMPLE 39

Preparation of (4R,5S)-5-(4-methylthiophenyl)-4-formyl-3-propionyl-2,2-dimethyl-1,3-oxazolidine (compound 29)

A solution of dimethylsulphoxide (2.8 g; 3.6 mmol) in methylene chloride (5 ml) was added to a solution of oxalyl chloride (1.8 g; 14.1 mmol) in methylene chloride (20 ml) kept at −60° C. under nitrogen. A solution of compound 28 (see Example 38) (4 g; 12.9 mmol) in methylene chloride (25 ml) was added after 30 minutes to the solution.

Triethylamine (9.6 g; 92.9 mmol) was added under stirring to the reaction mixture kept at −60° C. for 30 minutes. The reaction mixture was kept at −60° C. for 15 minutes, then it was heated to 0° C. in 1 hour and poured into a 5% sodium bicarbonate solution (80 ml). The aqueous phase was extracted with methylene chloride (30 ml); the combined organic phases were dried over sodium sulphate and evaporated under vacuum to give an oily residue (Compound 29) (3.9 g) which was used in the next step (Example 40).

EXAMPLE 40

Preparation of (4S,5S)-5-(4-methylthiophenyl)-4-formyl-3-propionyl-2,2-dimethyl-1,3-oxazolidine (compound 30)

1,4-Diazabicyclo-[2,2,2]-octane (0.13 g; 1.17 mmol) was added to compound 29 (3.6 g; 11.7 mmol) (see Example 39) kept under mechanical stirring at 40° C. under nitrogen.

The reaction was monitored by $^1$H-NMR (300 MHz); as soon as the ratio 30:29 was equal to 40:60, crystals of compound 30 (10 mg) were added to the reaction mixture.

At the end of the reaction (ratio 29:30=14:86) the suspension was dissolved into a solution of acetic acid (0.071 g; 1.18 mmol) in methylene chloride (10 ml). The organic phase was washed with water, dried over sodium sulphate and evaporated under vacuum. A residue (3.5 g) was obtained which was crystallized from isopropanol/isopropyl ether at −10° C. to give pure compound 30 formed by two rotamers ($^1$H-NMR in CDCl$_3$):

Major rotamer $^1$H-NMR (CDCl$_3$): δ (ppm): 1.08 (part X of an ABX$_3$ system, J=7.3 Hz); 1.73 (s, 3H); 1.86 (s, 3H); 1.99 (part A of an ABX$_3$ system, J=7.3 Hz, J=16 Hz, 2H); 2.16 (part B of an ABX$_3$ system, J=7.3 Hz, J=16 Hz, 2H); 2.48 (s, 3H); 4.49 (dd, J=2.8 Hz, J=6.4 Hz, 1H); 5.44 (d, J=6.4 Hz, 1H); 7.26 (AA'BB' system, Δν=22 Hz, 4H); 9.17 (d, J=2.9 Hz, 1H).

Minor rotamer $^1$H-NMR (CDCl$_3$): δ (ppm): 1.2 (t, 3H, J=7.3 Hz); 1.6 (s, 3H); 1.89 (s, 3H); 2.1 (m, Δν=60 Hz, 2H); 2.47 (s, 3H); 5.01 (d, J=7.1 Hz, 1H); 5.36 (d, J=7.1 Hz, 1H); 7.27 (AA'BB' system, Δν=22 Hz, 4H); 9.06 (s, 1H).

EXAMPLE 41

Preparation of threo-(2R,3S)-3-hydroxy-3-(4-methylthiophenyl)-2-acetamido propionic acid methyl ester (Compound 31)

A solution of (2R,3S)-3-hydroxy-3-(4-methylthiophenyl)-2-acetamido propionic acid (1.5 g; 5.5 mmol) (prepared according to the procedure described in Italian Patent No. 1,196,434), anhydrous p-toluenesulphonic acid (0.032 g; 0.18 mmol) and trimethylorthoformate (0.18 g; 1.68 mmol) in methyl alcohol (15 ml) was stirred under nitrogen at 25° C. for 16 hours. The reaction mixture was filtered to give compound 31 (solid A), while the mother liquors were evaporated under vacuum to give a residue (1.2 g). A 5% sodium bicarbonate aqueous solution (5 ml) was added to the residue and the mixture was stirred for 10 minutes.

The heterogeneous mixture was filtered, the insoluble (solid B) was washed with water (5 ml) and then with acetone (5 ml). The combined solids (A and B) (0.8 g; 2.82 mmol; 51% yield) were crystallized from ethyl alcohol to give pure compound 31.

$[α]_D^{25}$ = −14.7° (c 0.17, CHCl$_3$)

m.p.=189°–191° C.

I.R. (KBr): 3361 cm$^{-1}$, 1756 cm$^{-1}$, 1650 cm$^{-1}$, 1530 cm$^{-1}$.

$^1$H-NMR (300 MHz, CDCl$_3$+D$_2$O): δ (ppm): 1.96 (s, 3H); 2.48 (s, 3H); 3.76 (s, 3H); 4.85 (dd, J=8.7 Hz, J=3.2 Hz, 1H); 5.23 (d, J=3.2 Hz, 1H); 6.23 (d, J=8.7 Hz, 1H); 7.21–7.29 (aromatic protons, 4H).

EXAMPLE 42

Preparation of (4R,5S)-5-(4-methylthiophenyl)-4-(methoxycarbonyl)-3-acetyl-2,2-dimethyl-1,3-oxazolidine (Compound 32)

2,2-Dimethoxypropane (21.6 g; 207 mmol) and anhydrous p-toluenesulphonic acid (0.087 g; 0.5 mmol) were added to a vigorously stirred mixture of compound 31 (2.5 g; 8 mmol) and acetone (5 ml) at 25° C. and under nitrogen.

The mixture was heated at 65° C. for 2.5 hours, cooled to 25° C., and poured into a mixture of 5% NaHCO$_3$ aqueous solution (40 ml) and methylene chloride (50 ml). The mixture was stirred at 25° C. for 10 minutes. The organic layer was separated, dried over Na$_2$SO$_4$ and evaporated under reduced pressure to give crude compound 32 (1.94 g). The crude product was purified by chromatography (silica gel, eluent ethylacetate) affording pure compound 32, which consists, on the base of $^1$H-NMR data, of two rotamers (restricted rotation of the amido group) in ratio 60:40.

I.R. (CCl$_4$): 1756 cm$^{-1}$, 1672 cm$^{-1}$, 1390 cm$^{-1}$.

Major rotamer (60%)

$^1$H-NMR (300 MHz, CDCl$_3$): δ (ppm): 1.69 (s, 3H); 1.78 (s, 3H); 1.91 (s, 3H); 2.49 (s, 3H); 3.81 (s, 3H); 4.35 (d, J=6.8 Hz, 1H); 5.10 (d, J=6.8 Hz, 1H); 7.25–7.33 (aromatic protons, 4H).

Minor rotamer (40%)

$^1$H-NMR (300 MHz, CDCl$_3$): δ (ppm): 1.78 (s, 3H); 2.19 (s, 3H); 2.48 (s, 3H); 3.74 (s, 3H); 4.41 (d, J=8.3 Hz, 1H); 5.01 (d, J=8.3 Hz, 1H); 7.15–7.25 (aromatic protons, 4H).

EXAMPLE 43

Preparation of (4S,5S)-5-(4-methylthiophenyl)-4-(methoxycarbonyl)-3-acetyl-2,2-dimethyl-1,3-oxazolidine (Compound 33)

Sodium methoxide (0.37 g; 6.8 mmol) was added to a solution of crude compound 32 (2 g) in methyl alcohol (10 ml); the reaction mixture was stirred at 40° C. under nitrogen for 72 hours. The reaction mixture was cooled to 25° C. and added under stirring with a mixture of 0.1N HCl (20 ml) and methylene chloride (30 ml).

The organic layer was separated and dried over $Na_2SO_4$ and evaporated under reduced pressure to give an oily residue (1.1 g) consisting of a mixture of compound 32 and compound 33 in 32:33=40:60 ratio ($^1$H-NMR).

Analytically pure compound 33, obtained by flash column chromatography (silica gel, eluent diethylether), was, on the base of $^1$H-NMR spectra in CDCl$_3$, a mixture of two rotamers due to restricted rotation of the amido group.

I.R. (CCl$_4$): 1758 cm$^{-1}$, 1672 cm$^{-1}$ 1398 cm$^{-1}$.

Major rotamer (82%)

$^1$H-NMR (300 MHz, CDCl$_3$): δ (ppm): 1.70 (s, 3H); 1.92 (s, 3H); 1.97 (s, 3H); 2.48 (s, 3H); 3.29 (s, 3H); 4.57 (d, J=6.6 Hz, 1H); 5.40 (d, J=6.6 Hz, 1H); 7.21–7.30 (aromatic protons, 4H).

Minor rotamer (18%)

$^1$H-NMR (300 MHz, CDCl$_3$): δ (ppm): 1.72 (s, 3H); 1.96 (s, 3H); 2.22 (s, 3H); 2.48 (s, 3H); 3.23 (s, 3H); 4.83 (d, J=6.6 Hz, 1H); 5.31 (d, J=6.6 Hz, 1H); 7.21–7.30 (aromatic protons, 4H).

EXAMPLE 44

Preparation of (4S,5S)-3-acetyl-2,2-dimethyl-4-hydroxymethyl-5-phenyl-1,3-oxazolidine (Compound 34)

A stirred mixture of enantiomerically pure (+)-(1S,2S)-2-amino-1-phenyl-1,3-propanediol (200 g; 1.19 mol), toluene (700 ml) and acetone (440 ml; 6 mol) was heated at reflux for 12 hours beneath a Dean Stark trap: a mixture of toluene, water and acetone was collected. The solvent was distilled under vacuum (internal temperature 80° C.) to give a residue (210 g).

Acetylchloride (82.5 g; 1.07 mol) was added in 1 hour at 0° C. to a stirred solution of the residue (200 g; 0.965 mol) and of triethylamine (108 g; 1.07 mol) in methylene chloride (800 ml). The reaction mixture was stirred for 3 hours at 15° C., then it was poured into water (300 ml). The organic phase was separated and the aqueous phase was extracted with methylene chloride (600 ml): the combined organic extracts were washed with 0.1N hydrochloric acid (300 ml) and then with water (300 ml), dried over sodium sulphate and concentrated under vacuum to give a residue (240 g), which, after crystallization from diethyl ether gave pure compound 34 (140 g; 0.57 mol; 59% yield).

Major rotamer:

$^1$H-NMR (300 MHz, DMSO+D$_2$O): δ (ppm): 1.46 (s, 3H); 1.49 (s, 3H); 2.05 (s, 3H); 3.56 (dd, J=11.48 Hz, J=4.0 Hz, 1H); 3.64 (dd, J=11.48 Hz, J=6.84 Hz, 1H); 4.08 (ddd, J=6.84 Hz, J=4.0 Hz, J=3.9 Hz, 1H); 5.09 (d, J=3.9 Hz, 1H); 7.30–7.46 (aromatic protons, 5H).

Minor rotamer:

$^1$H-NMR (300 MHz, DMSO+D$_2$O): δ (ppm): 1.58 (s, 3H); 1.65 (s, 3H); 2.05 (s, 3H); 3.82 (broad signal, 2H); 4.23 (broad signal, 1H); 5.09 (broad signal, 1H); 7.30–7.46 (aromatic protons, 5H).

EXAMPLE 45

Preparation of (4R,5S)-5-phenyl-4-formyl-3-acetyl-2,2-dimethyl-1,3-oxazolidine (Compound 35)

A mixture of (4S,5S)-5-phenyl-4-hydroxymethyl-3-acetyl-2,2-dimethyl-1,3-oxazolidine (5 g; 20 mmol), methylene chloride (20 ml), 2,2,6,6-tetramethylpiperidinyl-1-oxy (TEMPO) (0.031 g; 0.2 mmol), potassium bromide (0.195 g; 2 mmol) and water (2 ml) was cooled to 0° C. (water-ice bath). The mixture, under vigorous stirring, was added dropwise in 30 minutes to a solution prepared by adding a 5% sodium bicarbonate aqueous solution and then 1N HCl to sodium hypochlorite (23.1 ml; 24.9 mmol) (the pH of the solution was 8.7). The mixture was stirred for 30 minutes at 0° C. and the reaction was followed by TLC (silica gel, ethyl acetate as eluent). The phases were separated, the aqueous phase was extracted with methylene chloride (3×10 ml), the combined organic extracts were washed with a 5% sodium bicarbonate aqueous solution (10 ml) and with water (10 ml). The organic phase was dried over sodium sulphate. Evaporation of the solvent under reduced pressure gave the oily aldehyde 35 (4.65 g; 18.8 mmol; 94% yield) which, on the base of $^1$H-NMR data, in chloroform, consists of two rotamers (restricted rotation of the amido group) in ratio 53:47.

I.R. (CCl$_4$): 1740 cm$^{-1}$, 1672 cm$^{-1}$, 1390 cm$^{-1}$.

Major rotamer (53%):

$^1$H-NMR (300 MHz, CDCl$_3$): δ (ppm): 1.69 (s, 3H); 1.81 (s, 3H); 2.22 (s, 3H); 4.48 (dd, J=8.8 Hz, J=2.7 Hz, 1H); 5.02 (d, J=8.8 Hz, 1H); 7.35–7.45 (aromatic protons, 5H); 9.60 (d, J=2.7 Hz, 1H).

Minor rotamer (47%):

$^1$H-NMR (300 MHz, CDCl$_3$): δ (ppm): 1.77 (s, 3H); 1.81 (s, 3H); 1.94 (s, 3H); 4.34 (dd, J=6.9 Hz, J=3.1 Hz, 1H); 5.14 (d, J=6.9 Hz, 1H); 7.35–7.45 (aromatic protons, 5H); 9.68 (d, J=3.1 Hz, 1H).

EXAMPLE 46

Preparation of (4S,5S)-5-phenyl-4-formyl-3-acetyl-2,2-dimethyl-1,3-oxazolidine (Compound 36)

An homogeneous mixture of 1,4-diazabicyclo-[2,2,2]-octane (DABCO) (0.197 g; 1.76 mmol) and compound 35 (4.36 g; 17.6 mmol) was stirred at 40° C. for 3 hours; the reaction mixture was kept under stirring for additional 2 hours at 15° C. [35:36=40:60 as determined after acidic removal DABCO (see below) by $^1$H-NMR in CDCl$_3$ on the base of integrals of the aldehydic protons].

The reaction mixture was poured into a vigorously stirred mixture of methylene chloride (30 ml) and of a solution prepared by diluting up to 15 ml 0.5N hydrochloric acid (3.6 ml).

The aqueous phase was extracted with methylene chloride (15 ml). The combined organic extracts were dried over sodium sulphate and evaporated under vacuum.

The residue (4.3 g) consisted of a mixture of compounds 35 and 36 in 35:36=40:60 ratio as determined by $^1$H-NMR analysis in CDCl$_3$ on the base of integrals of aldehydic protons.

Compound 36

Major rotamer:

$^1$H-NMR (300 MHz, CDCl$_3$): δ (ppm): 1.75 (s, 3H); 1.87 (s, 3H); 1.94 (s, 3H); 4.52 (dd, J=6.4 Hz, J=2.7 Hz, 1H); 5.51 (d, J=6.4 Hz, 1H); 7.35–7.45 (aromatic protons, 5H); 9.15 (d, J=2.7 Hz, 1H).

Minor rotamer:
1H-NMR (300 MHz, CDCl₃): δ (ppm): 1.65 (s, 3H); 1.91 (s, 3H); 2.24 (s, 3H); 5.05 (broad d, J=7.0 Hz, 1H); 5.41 (d, J=7.0 Hz, 1H); 7.3–7.5 (aromatic protons, 5H); 9.03 (broad s, 1H).

EXAMPLE 47

Preparation of
(4R,5R)-5-(4-methylthiophenyl)-4-acetoxymethyl-2-methyl-1,3-oxazoline as p-toluenesulphonic salt (Compound 37) and of
(2R,3R)-3-(4-methylthiophenyl)-2-amino-1,3-propanediol [(2R,3R)-thiomicamine]

Anhydrous p-toluenesulphonic acid (3.9 g; 22.7 mmol) was added dropwise at 25° C. to a stirred solution of acetic anhydride (3.35 g; 32.8 mmol), acetic acid (1 g; 16.6 mmol) and (4R,5S)-5-(4-methylthiophenyl)-4-hydroxymethyl-3-acetyl-2,2-dimethyl-1,3-oxazolidine (Compound 6) (5 g; 16.9 mmol).

The reaction mixture was then heated to 35° C. and kept at this temperature for 4 hours. Removal of acetone under vacuum and cooling to 15° C. gave a solution of (4R,5R)-5-(4-methylthiophenyl)-4-acetoxymethyl-2-methyl-1,3-oxazoline as p-toluenesulphonic salt (compound 37) and of p-toluenesulphonic acid, acetone and acetic acid.

1H-NMR (300 MHz, CDCl₃): δ (ppm): 2.17 (s, 3H); 2.21 (s, 3H); 2.47 (s, 3H); 2.61 (s, 3H); 4.42 (dd, J=5.3 Hz, J=12.1 Hz, 1H); 4.46 (dd, J=4.3 Hz, J=12.1 Hz, 1H); 4.80 (ddd, J=5.3 Hz, J=4.3 Hz, J=8.1 Hz, 1H); 5.79 (d, J=8.1 Hz, 1H); 7.22–7.35 (aromatic protons, 4H); 7.18–7.67 (aromatic protons, 4H).

The crude product was slowly added at 15° C. to a solution of sodium hydroxide (5 g) in water (20 ml) and the reaction mixture was then heated to 98° C. and kept at 98° C. for 4.5 hours.

Cooling the solution to 15° C. in 2 hours caused the precipitation of (2R,3R)-thiomicamine which was filtered, washed with water and dried under vacuum at 60° C. Pure (2R,3R)-thiomicamine was obtained (3.05 g; 81% yield)

$[\alpha]_D^{20} = -33.8°$ (c 2, 0.2N HCl)

EXAMPLE 48

Preparation of
(4R,5S)-5-(4-methylthiophenyl)-3-acetyl-4-acetoxymethyl-2,2-dimethyl-1,3-oxazolidine (Compound 26)

Acetylchloride (3.2 g, 40.8 mmol) was added in 1 hour at 25° C. to a stirred solution of compound 6 (10 g; 33.9 mmol) and of triethylamine (4.2 g; 41.6 mmol) in methylene chloride (60 ml). The reaction mixture was stirred for 2 hours at 25° C., then it was poured into water (50 ml). The organic phase was separated and the aqueous phase was extracted with methylene chloride (100 ml): the combined organic extracts were washed with water (50 ml), dried over sodium sulphate and concentrated under vacuum to give a residue (11.4 g), which was purified by chromatography on silica gel (eluent: ethyl acetate/hexane=1:1) to give pure compound 26 (10.2 g; 30.2 mmol; 89% yield).

1H-NMR (300 MHz, DMSO): δ (s, 3H); 1.62 (s, 3H); 1.73 (s, 3H); 2.10 (s, 3H); 2.47 (s, 3H); 3.70 (dd, J=5.67 Hz, J=11.63 Hz, 1H); 3.78 (dd, J=6.64 Hz, J=11.63 Hz, 1H); 4.53 (ddd, J=5.12 Hz, J=6.64 Hz, J=5.67 Hz, 1H); 5.35 (d, J=5.12 Hz, 1H); 7.22–7.36 (aromatic protons, 4H).

EXAMPLE 49

Preparation of
(4S,5S)-5-(4-methylsulphonylphenyl)-3-acetyl-4-hydroxymethyl-2,2-dimethyl-1,3-oxazolidine (Compound 38)

A solution of 42% hydrogen peroxyde (2.5 ml; 30 mmol) was added in 1 hour, under stirring at 50° C., to a solution of compound 3 (2.95 g; 10 mmol), sodium tungstate dihydrate (11 mg) and EDTA (5 mg) in methanol (5 ml). The mixture was kept at 50° C. for 1 hour. After evaporation of the solvent under vacuum, the residue was treated with a mixture of methylene chloride (30 ml) and water (30 ml). The phases were separated and the organic phase was dried over sodium sulphate and evaporated under vacuum to give crude compound 38 (2.8 g).

Major rotamer:
1H-NMR (300 MHz, CDCl₃+D₂O): δ (ppm): 1.68 (s, 3H); 1.78 (s, 3H); 2.23 (s, 3H); 3.05 (s, 3H); 3.72 (dd, J=5.64 Hz, J=12.0 Hz, 1H); 3.84 (dd, J=12.0 Hz, J=3.23 Hz, 1H); 4.03 (ddd, J=8.62 Hz, J=5.64 Hz, J=3.23 Hz, 1H); 4.82 (d, J=8.60 Hz, 1H); 7.60–7.80 (aromatic protons, 4H).

Minor rotamer:
1H-NMR (300 MHz, CDCl₃+D₂O): δ (ppm): 1.54 (s, 3H); 1.68 (s, 3H); 2.11 (s, 3H); 3.05 (s, 3H); 3.84 (m, 2H); 4.03 (m, 1H); 5.31 (d, J=3.71 Hz, 1H); 7.60–7.80 (aromatic protons, 4H).

EXAMPLE 50

Preparation of
(4R,5S)-5-(4-methylsulphonylphenyl)-3-acetyl-4-formyl-2,2-dimethyl-1,3-oxazolidine (Compound 39)

A solution of m-chloroperbenzoic acid (assay 75%, 24.5 g; 115 mmol) in methylene chloride (25 ml) was added in 1 hour, under stirring at 25° C., to a solution of compound 4 (15.3 g; 52.3 mmol), in methylene chloride (190 ml). The mixture was kept at 25° C. for 2 hours, then poured in 5% sodium bicarbonate aqueous solution (100 ml). After separation of the phases, the organic phase was washed with water (50 ml), dried over sodium sulphate and evaporated under vacuum to give crude compound 39 (10.5 g; 32.4 mmol; 62% yield).

Major rotamer
1H-NMR (300 MHz, CDCl₃): δ (ppm): 1.78 (s, 3H); 1.83 (s, 3H); 2.25 (s, 3H); 3.07 (s, 3H); 4.40 (dd, J=2.39, J=8.49, 1H); 5.11 (d, J=8.49, 1H); 9.61 (d, J=2.39, 1H); 7.55–8.05 (aromatic protons, 4H).

Minor rotamer
1H-NMR (300 MHz, CDCl₃): δ (ppm): 1.71 (s, 3H); 1.83 (s, 3H); 2.25 (s, 3H); 3.07 (s, 3H); 4.28 (dd, J=2.74, J=6.73, 1H); 5.24 (d, J=6.73, 1H); 9.73 (d, J=2.74, 1H); 7.55–8.05 (aromatic protons, 4H).

EXAMPLE 51

Preparation of
(4S,5S)-5-(4-methylsulphonylphenyl)-3-acetyl-4-formyl-2,2-dimethyl-1,3-oxazolidine (Compound 40)

1,4-Diazabicyclo-[2,2,2]-octane (35 mg; 0.3 mmol) was added under stirring at 40° C. to a solution of compound 39 (1 g; 3 mmol) in toluene (0.5 ml). After 20 hours a diastereomeric ratio 40:39=48:52 was reached (as determined via 1H-NMR on the solution).

EXAMPLE 52

Preparation of
(4S,5S)-5-(4-methylsulphonylphenyl)-3-acetyl-4-formyl-2,2-dimethyl-1,3-oxazolidine (Compound 40)

A solution of m-chloroperbenzoic acid (assay 3.2 g; 15 mmol) in methylene chloride (15 ml) was added in 1 hour, under stirring at 25° C., to a solution of compound 5 (2 g; 6.8 mmol), in methylene chloride (15 ml). The mixture was kept at 25° C. for 2 hours, then poured in 5% sodium bicarbonate aqueous solution (15 ml). After separation of the phases, the organic phase was washed with water (15 ml), dried over sodium sulphate and evaporated under vacuum to give crude compound 40 (1.8 g; 90% yield). Pure compound 40 was obtained by chromatography on silica gel (eluent: ethyl acetate).

Major rotamer:
$^1$H-NMR (300 MHz, CDCl$_3$): δ (ppm): 1.76 (s, 3H); 1.87 (s, 3H); 1.96 (s, 3H); 3.07 (s, 3H); 4.59 (dd, J=6.21 Hz, J=3.04 Hz, 1H); 5.58 (d, J=6.21 Hz, 1H); 7.60-8.10 (aromatic protons, 4H); 9.16 (d, J=3.04 Hz, 1H).

Minor rotamer:
$^1$H-NMR (300 MHz, CDCl$_3$): δ (ppm): 1.66 (s, 3H); 1.87 (s, 3H); 1.93 (s, 3H); 3.09 (s, 3H); 5.08 (dd, J=7.08 Hz, J=1.60 Hz, 1H); 5.49 (d, J=7.08 Hz, 1H); 7.60-8.10 (aromatic protons, 4H); 9.05 (d, J=1.60 Hz, 1H).

EXAMPLE 53

Preparation of enantiomerically pure
(+)-(2S,3S)-Thiomicamine

Enantiomerically pure (+)-thiomicamine was obtained in 90% yield by crystallization of crude (+)-thiomicamine (50 g; e.e. 90%) from isopropanol (1000 ml).
$[α]_D^{20}$= +33.2° (c 2, 0.1N HCl)—m.p. 151°-152° C.
$^1$H-NMR (300 MHz, DMSO-D$_2$O): δ (ppm): 2.43 (s, 3H); 2.64 (ddd, J=6.35, J=6.10, J=4.88, 1H); 3.09 (dd, J=10.50, J=6.35, 1H); 3.38 (dd, J=10.50, J=4.88, 1H); 4.37 (d, J=6.1, 1H); 7.21 (4H, aromatics).
$^{13}$C-NMR (DMSO-D$_2$O): 15.01, 59.00, 63.08, 72.76, 125.70, 127.17, 136.02, 141.07.

EXAMPLE 54

(4S,5S)-5-(4-methylthiophenyl)-4-hydroxymethyl-3-acetyl-2,2-dimethyl-1,3-oxazolidine (Compound 3)

A stirred mixture of enantiomerically pure (+)-thiomicamine (100 g; 0.469 mol), toluene (920 ml) and acetone (100 ml) was heated at reflux for 18 hours beneath a Dean Stark trap: a mixture of toluene, water and acetone (11 g) was collected. The solvent (200 ml) was distilled at ambient pressure and then under vacuum (internal temperature 80° C.) to give compound 7 (118.6 g) as residue.

$^1$H-NMR (300 MHz, DMSO): δ (ppm): 1.47 (s, 3H); 1.50 (s, 3H); 2.47 (s, 3H); 3.09 (ddd, J=5.67, 4.17 and 11.4, 1H); 3.70 (ddd, J=5.67, 6.64 and 11.4, 1H); 4.06 (ddd, J=3.84, 6.64 and 4.17, 1H); 5.06 (d, J=3.84, 1H); 5.24 (t, J=5.67, 1H); 7.21-7.27 (aromatic protons, 4H).

Acetylchloride (38.3 g; 0.49 mol) was added in 1 hour at 15° C. to a stirred solution of crude compound 7 and of triethylamine (70.6 g; 0.7 mol) in methylene chloride (1170 ml). The reaction mixture was stirred for 12 hours at 15° C., then it was poured into 0.5N hydrochloric acid (750 ml). The organic phase was separated and the aqueous phase was extracted with methylene chloride (300 ml): the combined organic extracts were washed with water (300 ml), dried over sodium sulphate and concentrated under vacuum to give a residue (120 g) which, after crystallization from methanol (140 ml), gave pure compound 3 (67.8 g; 0.23 mol; 49% yield).

$^1$H-NMR (300 MHz, DMSO): δ (ppm): 1.47 (s, 3H); 1.50 (s, 3H); 2.06 (s, 3H); 2.47 (s, 3H); 3.55 (ddd, J=5.7, 11.5 and 4.0, 1H); 3.61 (ddd, J=5.7, 11.5 and 6.8, 1H); 4.06 (ddd, J=3.8, 4.0 and 6.8, 1H); 5.07 (d, J=3.8, 1H); 5.24 (t, J=5.7, 1H); 7.27-7.41 (aromatic protons, 4H).
$^{13}$C-NMR (DMSO): 166.7; 137.7; 137.2; 127.2; 125.8; 95.2; 78.3; 64.6; 61.1; 26.8; 26.24; 23.5; 14.6.
$[α]_D^{20}$= +16.9° (c 1.0, CHCl$_3$)
I.R. (KBr): 3280, 1630 cm$^{-1}$.
M.p.=142°-145° C.
MS: m/e (rel. intensity): 296 (M+1; 100), 280 (11), 238 (39).

EXAMPLE 55

Preparation of
(4R,5S)-5-(4-methylthiophenyl)-4-formyl-3-acetyl-2,2-dimethyl-1,3-oxazolidine (Compound 4)

A solution of dimethylsulphoxide (40.3 g; 0.51 mol) in methylene chloride (100 ml) was added in 30 minutes at −60° C. under nitrogen to a stirred solution of oxalyl chloride (26.2 g; 0.21 mol) in methylene chloride (100 ml). The solution was stirred at −60° C. for 30 minutes. A solution of compound 3 (50.9 g; 0.17 mol) in methylene chloride (600 ml) was added dropwise in 30 minutes at −60° C. to the previously prepared solution. The reaction mixture was kept under stirring at −60° C. for 15 minutes and then warmed up to −50° C. Triethylamine (91.0 g; 0.96 mol) was added under stirring in 20 minutes to the solution kept at −50° C. The reaction mixture was allowed to warm up to 0° C. in 2 hours and then it was poured into a 10% ammonium chloride aqueous solution (300 ml). The organic phase was separated and aqueous phase was extracted with methylene chloride (200 ml); the combined organic extracts were washed with water (200 ml), dried over sodium sulphate and the solvent was evaporated under vacuum to give oily crude compound 4 (51.5 g) (HPLC assay >95% determined as compound 3 after reduction with sodium borohydride, yield ≧95%), which consisted, on the basis of the $^1$H-NMR data, of two rotamers in ration 56:44.

Major rotamer:
$^1$H-NMR (300 MHz, CDCl$_3$): δ (ppm): 1.74 (s, 3H); 1.70 (s, 3H); 2.16 (s, 3H); 2.42 (s, 3H); 4.35 (dd, J=8.79 and 2.91, 1H); 4.91 (d, J=8.79, 1H); 7.19-7.24 (aromatic protons, 4H); 9.50 (d, J=2.91, 1H).

Minor rotamer:
$^1$H-NMR (300 MHz, CDCl$_3$): δ (ppm): 1.62 (s, 3H); 1.74 (s, 3H); 1.88 (s, 3H); 2.43 (s, 3H); 4.28 (dd, J=6.83 and 2.93, 1H); 5.06 (d, J=6.83, 1H); 7.27-7.30 (aromatic protons, 4H); 9.61 (d, J=2.93, 1H).

Rotamers mixture:
$^{13}$C-NMR (74.5 MHz, CDCl$_3$): δ (ppm): 15.45; 21.59; 24.12; 24.54; 26.17; 26.32; 28.08; 71.10; 72.42; 75.20; 76.16; 93.94; 97.58; 126.85; 126.67; 126.54; 133.55; 132.78; 139.56; 139.77; 167.17; 195.64; 196.56.
I.R. (CCl$_4$): 2980, 1742, 1732, 1673 cm$^{-1}$.
MS: m/e (rel.intensity): 294 (M+1; 78), 236 (100).

EXAMPLE 56

Preparation of
(4S,5S)-5-(4-methylthiophenyl)-4-formyl-3-acetyl-2,2-dimethyl-1,3-oxazolidine (Compound 5)

An homogeneous mixture of 1,4-diazabicyclo-[2,2,2]-octane (1.44 g; 12.8 mmol) and the crude product 4 (51.5 g) was stirred at 40° C. The mixture, which became heterogeneous (after 3 hours compound 5 started to crystallize from the reaction mixture), was cooled to 35° C. and then stirred for 2 hours at 35° C. The almost solid mixture was cooled to 25° C. and kept at 25° C. for 3 hours [4:5=5:95 as determined after acidic removal of DABCO (see below) by $^1$H-NMR in CDCl$_3$ on the base of integrals of aldehydic protons]. The reaction mixture was poured into a vigorously stirred mixture of methylene chloride (150 ml) and of a solution prepared by diluting up to 100 ml 0.5N hydrochloric acid (26 ml). The aqueous phase was extracted with methylene chloride (150 ml). The combined organic extracts were dried over sodium sulphate and evaporated under vacuum. The residue (51 g) consisted of a mixture of 4 and 5 in the ratio 4:5=5:95 as determined by $^1$H-NMR. The residue was crystallized from 4-t-butyltoluene (100 ml) affording pure 5 (38.5 g; 0.13 mol; 76% yield calculated on compound 3).

Major rotamer:
$^1$H-NMR (300 MHz, CDCl$_3$): δ (ppm): 1.73 (s, 3H); 1.85 (s, 3H); 1.93 (s, 3H); 2.48 (s, 3H); 4.49 (dd, J=2.8 and 6.4, 1H); 5.46 (d, J=6.4, 1H); 7.23–7.31 (aromatic protons, 4H); 9.17 (d, J=2.8, 1H).

Minor rotamer:
$^1$H-NMR (300 MHz, CDCl$_3$): δ (ppm): 1.64 (s, 3H); 1.89 (s, 3H); 2.23 (s, 3H); 2.47 (s, 3H); 5.00 (dd, J=7.0, 1H); 5.36 (d, J=7.0, 1H); 7.23–7.31 (aromatic protons, 4H); 9.06 (s broad, 1H).

Major rotamer:
$^{13}$C-NMR (74.5 MHz, CDCl$_3$): δ (ppm): 15.26; 23.67; 25.92; 69.22; 77.06; 95.99; 126.39; 129.44; 139.54; 164.41; 196.58.

$[α]_D^{20}$ = +124.3° (c 1, CHCl$_3$)
M.p.=97°–102° C.
I.R. (Kbr): 1735, 1660, 1645 cm$^{-1}$
MS m/e (rel.intensity): 294 (M+1; 100), 236 (35), 153 (20).

EXAMPLE 57

DABCO catalyzed epimerization of compound 4 (or 5) in toluene

A solution of 4 (2.95 g; 10.04 mmol), 1,4-diazabicyclo-[2,2,2]-octane (44.9 mg; 0.4 mmol) in toluene (29.5 ml) was stirred at 60° C. for 24 hours. $^1$H-NMR analysis of the solution [4-methylthiobenzaldehyde (380 mg; 2.5 mmol; internal standard)] showed the present of 4 and 5 in ratio 45:55, [(4+5) accounts for 94% of the starting 4]. The same result was obtained starting from 5.

EXAMPLE 58

Preparation of compound 6

Sodium borohydride (4.9 g; 0.13 mol) was added at 5° C. to a stirred mixture of calcium chloride (14.3 g; 0.13 mol) and of a solution of 5 (53.7 g; 0.18 mol) and of tetrahydrofuran (220 ml) in ethanol (570 ml). The mixture was stirred for 2 hours at 5° C. and then poured into a mixture of pH 7.00 aqueous solution (300 ml, 0.05M K$_2$HPO$_4$ adjusted to pH 7.00 with H$_3$PO$_4$) and methylene chloride (400 ml). The aqueous phase was extracted with methylene chloride (300 ml), the combined organic extracts were dried over sodium sulphate and the solvent evaporated under vacuum to give the crude compound 6 (54.7 g; HPLC assay 96%, yield 97%). Analytically pure 6 was obtained by crystallization of the crude 6 from toluene. $^1$H-NMR (300 MHz, DMSO): δ (ppm): 1.58 (s, 3H); 1.62 (s, 3H); 2.10 (s, 3H); 2.46 (s, 3H); 3.03 (ddd, J=11.2, 5.1 and 5.3, 1H); 3.18 (ddd, J=11.2, 8.0 and 5.3, 1H); 4.25 (ddd, J=5.0, 8.0 and 5.1, 1H); 4.65 (t, J=5.3, 1H); 5.25 (d, J=5.0, 1H); 7.22–7.32 (aromatic protons, 4H).

$^{13}$C-NMR (74.5 MHz, DMSO): δ (ppm): q 14.66; q 23.65; q 24.07; q 27.01; t 60.65; d 61.85; d 76.34; d 93.33; d 125.55; d 126.65; s132.44; s 137.22; s 167.70.

$[α]_D^{20}$ = +80.8° (c 1.0, CHCl$_3$)
I.R. (KBr): 3320, 1630 cm$^{-1}$.
M.p. =123°–128° C.
MS: m/e (rel.intensity): 296.1 (M+1; 100), 238.1 (60), 220 (11).

EXAMPLE 59

Preparation of enantiomerically pure (+)-(2R,3S)-2-amino-3-(methylthiophenyl)-1,3-propanediol [(2R,3S)-Thiomicamine]

Sodium hydroxide (1.76 g; 44 mmol) was added at room temperature to a suspension of crude 6 (10 g; 33.9 mmol) in water (17 ml); the suspension was heated at reflux for 8 hours. The solution was added with water (25 ml) and cooled in 1 hour to 15° C. The heterogeneous mixture was filtered, the insoluble washed with water (15 ml) and dried under vacuum to give crude (2R,3S)-thiomicamine (6.65 g). Crystallization from toluene gave the enantiomerically pure compound (6.0 g; 83% yield).

$^1$H-NMR (300 MHz, DMSO-D$_2$O): δ (ppm): 2.45 (s, 3H); 2.78 (ddd, J=7.00, J=6.23, J=4.54, 1H); 3.26 (dd, J=10.44, J=7.00, 1H); 3.38 (dd, J=10.44, J=4.54, 1H); 4.37 (d, J=6.23, 1H); 7.23–7.28 (4H, aromatics).

$^{13}$C-NMR (74.5 MHz, DMSO-D$_2$O): δ (ppm): 14.96; 58.24; 63.03; 74.16; 125.60; 127.56; 136.12; 140.28.
$[α]_D^{20}$ = −32.8° (c 2, HCl 0.1 N)
M.p.=117°–119° C.

EXAMPLE 60

Preparation of (−)-(2R,3R)-3-(4-methylthiophenyl)-2-amino-1,3-propanediol [(2R,3R)-Thiomicamine]

p-Toluenesulphonic acid monohydrated (20 g; 105 mmol) was added at 25° C. under stirring to a suspension of the crude 6 (10 g; 33.9 mmol) in water (60 ml). The suspension was heated to 75° C. and kept at 75° C. for 2.5 hours to give a solution which was heated to 95° C. and kept at 95° C. for 42 hours [ratio (2R,3R):(2R,3S)-thiomicamine=67:33]. Cooling the solution to 15° C. caused the precipitation of a mixture of (−)-(1R,2R)-thiomicamine and compound as p-toluenesulphonates. After 1 hour at 15° C. the salts were filtered and washed with water (20 ml); aqueous washings were combined together with mother liquors and saved (solution A). Sodium hydroxide (1.2 g; 30 mmol) was added at 25° C. to a stirred suspension of the p-toluenesulphonates (12.1 g; (2R,3R):(2R,3S)-thiomicamine=76:24) in water (40 ml) up to pH 10.5. The solution was cooled to 5° C., the insoluble was filtered, washed with water (20 ml) and dried under vacuum; aqueous washing were combined with the mother liquors (solution B). The solid thiomicamine (4.3 g; HPLC assay 97%, (2R,3R):(2R,3S)-thiomicamine=96:4) was crystallized from isopropanol (100 ml) at 5° C. to give analytically pure (2R,3R)-thiomicamine (3.4 g; yield 47%; $[α]_D^{20}$ = −33.2° (c 2, 0.1N HCl); e.e. >99%).

Recycling of mother liquors: evaporation of the solvent from solution B at 50° C. gave a residue (7.5 g;

containing 1.74 g of (2R,3R) and (2R,3S)-thiomicamine in the ratio 84:16) which was suspended into propan-2-ol (50 ml). The reaction mixture was heated to reflux and filtered; the resulting solution was evaporated under reduced pressure to give a residue (2.3 g containing 1.64 g of (2R,3S) and (2R,3R)-thiomicamine in the ratio 84:16). The residue was combined with solution A (85.2 g) and the solution was concentrated to 50 g under vacuum at 50° C. The mixture was heated under stirring at 90° C. for 24 hours (ratio (2R,3S):(2R,3R)-thiomicamine=34:66; 2.36 g). The solution was cooled to 15° C. and the insoluble was filtered, dissolved at 25° C. under stirring in an aqueous solution of sodium hydroxide (0.3 g; 7.5 mmol) in water (12 ml). The solution, having pH 10.5, was heated as above to give crude thiomicamine (1.1 g; (2R,3R)-thiomicamine; d.e. >98.5%) which was crystallized from isopropanol to give pure (−)-(2R,3R)-thiomicamine (1.06 g; 15% yield; overall yield 62%)

$[\alpha]_D^{20} = -33.8°$ (c 2, 0.1N HCl)

EXAMPLE 61

Acidic equilibration of (−)-(2R,3R)-thiomicamine

A solution of (2R,3R)-thiomicamine (10.0 g; 46.9 mmol) and p-toluenesulphonic acid monohydrated (20.0 g; 105.0 mmol) in water (60 ml) was heated at 100° C. for 48 hours. HPLC analysis of the solution showed a ratio (2R,3R):(2R,3S)-thiomicamine=69:31, the total amount accounting for 87% of the starting (2R,3R)-thiomicamine.

EXAMPLE 62

Preparation of (4R,5S)-5-(4-methylsulphonylphenyl)-3-acetyl-4-formyl-2,2-dimethyl-1,3-oxazolidine (Compound 39)

A mixture of compound 38 (1 g; 3 mmol), methylene chloride (7.5 ml), 2,2,6,6-tetramethylpiperidinyl-1-oxy (TEMPO) (6.15 mg), potassium bromide (40 mg) was cooled to 0° C. (water-ice bath). The mixture, under vigorous stirring, was added dropwise in 30 minutes to a solution prepared by adding a 8% sodium bicarbonate aqueous solution (15 ml) and then 1N HCl to sodium hypochlorite (3.7 ml; 7.8% w/v) (the pH of the solution was 8.7). The mixture was stirred for 30 minutes at 0° C. and the reaction was followed by TLC (silica gel, ethyl acetate as eluent). The phases were separated, the aqueous phase was extracted with methylene chloride (3×10 ml), the combined organic extracts were washed with a 5% sodium bicarbonate aqueous solution (10 ml) and with water (10 ml). The organic phase was dried over sodium sulphate. Evaporation of the solvent under vacuum gave compound 39 (0.41 g) as residue.

EXAMPLE 63

Preparation of compound 6 from a mixture of compounds 4 and 5 (ratio 5:4=50:50)

A mixture of compounds 5 and 4 (10 g; 34 mmol) (5:4=50:50) was added to a solution of citric acid (0.25 g) in ethanol (38 g). Sodium borohydride (0.15 g; 3.94 mmol) was added in two portion (the second after 15 minutes) under stirring for 20 minutes and then was poured into a pH 7 buffered aqueous solution (30 ml) and extracted with methylene chloride (30 ml). The combined organic extracts were washed with water and the solvent was removed under vacuum to give a crude (10.7 g).

A mixture of 3 and 6 (2.04 g in the ratio 6:3=84:16) and a mixture of 4 and 5 (6.7 g in the ratio 4:5=60:40) was obtained after usual work up.

EXAMPLE 64

Preparation of compound 4 p-Toluenesulphonylchloride (3.8 g; 0.02 mol) was added portionwise to a cold mixture (0° C.) of compound 3 (2.95 g; 0.01 mol), dimethylsulphoxide (4.5 g; 0.058 mol) and toluene (7.5 ml).

The mixture was kept at 0° C. for 0.5 hours. Triethylamine (4 g; 0.04 mol) was added dropwise at 0° C. and 5° C. under stirring in 1 hour to the mixture. The reaction mixture was kept at 0° C. for 2 hours and then poured into water (20 ml). The organic phase was washed with 0.1N hydrochloric acid (20 ml) and evaporated under vacuum to give a residue (2.8 g) containing compound 4 (2.3 g).

EXAMPLE 65

Preparation of compound 4

Benzenesulphonylchloride (3.5 g; 0.02 mol) was added portionwise to a cold mixture (0° C.) of compound 3 (2.95 g; 0.01 mol), dimethylsulphoxide (6 g; 0.077 mol) and toluene (7.5 ml).

The mixture was kept at 0° C. for 0.5 hours. Triethylamine (4 g; 0.04 mol) was added dropwise at 0° C. and 10° C. under stirring in 1 hour to the mixture. The reaction mixture was kept at 0° C. for 2 hours and then poured into water (20 ml). The organic phase was washed with 0.1N hydrochloric acid (20 ml) and evaporated under vacuum to give a residue (2.7 g) containing compound 4 (2.05 g).

EXAMPLE 66

Preparation of compound 4

2,4,6-Triisopropylbenzenesulphonylchloride (4.55 g; 0.015 mol) was added portionwise to a cold mixture (−10° C.) of compound 3 (2.95 g; 0.01 mol), dimethysulphoxide (3.2 g; 0.04 mol) and methylene chloride (8 ml).

The mixture was kept at −5° C. for 0.5 hours. Triethylamine (3 g; 0.03 mol) was added dropwise at −5° C. under stirring in 30 minutes to the mixture. The reaction mixture was heated to 15° C. and kept at 15° C. under stirring for 4 hours. The mixture was then poured into water (20 ml). The organic phase was evaporated under vacuum to give a residue (8 g) containing compound 4 (2 g).

EXAMPLE 67

Preparation of compound 4

2-Mesitylenesulphonylchloride (3.3 g; 0.015 mol) was added portionwise to a cold mixture (−10° C.) of compound 3 (2.95 g; 0.01 mol), dimethylsulphoxide (3.2 g; 0.04 mol) and methylene chloride (8 ml). The mixture was kept at −5° C. for 0.5 hours. Triethylamine (3 g; 0.03 mol) was added dropwise at −5° C. and 0° C. under stirring in 30 minutes to the mixture. The reaction mixture was kept at 0° C. under stirring for 4 hours. The mixture was then poured into water (20 ml). The organic phase was evaporated under vacuum to give a residue (4.2 g) containing compound 4 (2 g).

What we claim is:

1. A compound of the formula

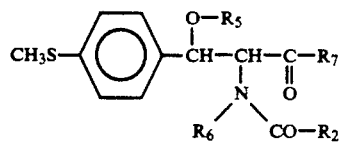
wherein $R_2$ represents a lower alkyl, dichloromethyl, phenyl, alkoxy or benzyloxy group; $R_5$ represents a lower alkyl or acyl group and $R_6$ a hydrogen atom, and $R_7$ represents a hydrogen atom.
2. The compound of claim 1 having the (2R,3S) configuration.
3. The compound of claim 1 having the (2S,3S) configuration.
* * * * *

UNITED STATES PATENT AND TRADEMARK OFFICE
CERTIFICATE OF CORRECTION

PATENT NO. : 5,284,966
DATED : February 8, 1994
INVENTOR(S) : Marco VILLA, et al It is certified that error appears in the above-identified patent and that said Letters Patent is hereby corrected as shown below:

On the title page, Item 30, Priority Data should be changed from "Oct. 22, 1989" to --Oct. 20, 1989--.

Signed and Sealed this

Twentieth Day of September, 1994

*Attest:*

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,284,966
DATED : February 8, 1994
INVENTOR(S) : Marco VILLA, et al It is certified that error appears in the above-identified patent and that said Letters Patent is hereby corrected as shown below:

Title Page, Item 54, Line 4 of the Title should be changed from "(SR,3R)" to --(2R,3R)--.

Signed and Sealed this

Twenty-ninth Day of November, 1994

Attest:

BRUCE LEHMAN

*Attesting Officer*    *Commissioner of Patents and Trademarks*